(12) United States Patent
Sabelle et al.

(10) Patent No.: US 8,585,779 B2
(45) Date of Patent: Nov. 19, 2013

(54) COMPOSITION COMPRISING AT LEAST ONE 2-PYRROLIDONE FUNCTIONALIZED IN THE 4 POSITION WITH A CARBOXYLIC ACID OR AMIDE, AND AT LEAST ONE DIRECT DYE OR A PIGMENT FOR DYEING KERATIN FIBRES

(75) Inventors: Stéphane Sabelle, Paris (FR); Madeleine Leduc, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/703,038

(22) PCT Filed: Jun. 8, 2011

(86) PCT No.: PCT/EP2011/059523
§ 371 (c)(1),
(2), (4) Date: Mar. 14, 2013

(87) PCT Pub. No.: WO2011/154460
PCT Pub. Date: Dec. 15, 2011

(65) Prior Publication Data
US 2013/0167307 A1    Jul. 4, 2013

Related U.S. Application Data

(60) Provisional application No. 61/357,650, filed on Jun. 23, 2010.

(30) Foreign Application Priority Data

Jun. 9, 2010 (FR) ...................................... 10 54557

(51) Int. Cl.
*A61Q 5/10* (2006.01)
*C07D 207/26* (2006.01)

(52) U.S. Cl.
USPC ............ 8/405; 8/435; 8/574; 8/680; 132/202; 132/208; 548/400

(58) Field of Classification Search
USPC .............. 8/405, 435, 574, 680; 132/202, 208; 548/400
See application file for complete search history.

(56) References Cited

U.S. PATENT DOCUMENTS

| | | | |
|---|---|---|---|
| 4,070,370 A | 1/1978 | Elliott et al. | |
| 4,823,985 A | 4/1989 | Grollier et al. | |
| 5,708,151 A | 1/1998 | Mockli | |
| 5,990,479 A | 11/1999 | Weiss et al. | |
| 6,106,577 A | 8/2000 | Audousset et al. | |
| 6,225,198 B1 | 5/2001 | Alivisatos et al. | |
| 8,067,651 B2 | 11/2011 | Leinweber et al. | |
| 2005/0065204 A1 | 3/2005 | Iding et al. | |
| 2009/0042747 A1 | 2/2009 | Leinweber et al. | |
| 2009/0163545 A1 | 6/2009 | Goldfarb | |
| 2009/0282624 A1 | 11/2009 | De Boni | |
| 2010/0143276 A1* | 6/2010 | Richard et al. .................. 424/60 |

FOREIGN PATENT DOCUMENTS

| | | |
|---|---|---|
| EP | 0714954 | 6/1996 |
| EP | 1184426 | 3/2002 |
| EP | 1342759 | 9/2003 |
| EP | 2022781 | 2/2009 |
| EP | 2028247 | 2/2009 |
| EP | 2095809 | 9/2009 |
| EP | 2193783 | 6/2010 |
| FR | 2243959 | 4/1976 |
| FR | 2586913 | 3/1987 |
| FR | 2679771 | 2/1993 |
| FR | 2741530 | 5/1997 |
| WO | 93/02655 | 2/1993 |
| WO | 95/01772 | 1/1995 |
| WO | 95/15144 | 6/1995 |
| WO | 01/62726 | 8/2001 |
| WO | 2007/140982 | 12/2007 |
| WO | 2008/131396 | 10/2008 |
| WO | 2010/039509 | 4/2010 |

OTHER PUBLICATIONS

STIC Search Report dated Apr. 22, 2013.*
International Search Report for PCT/EP2011/059523.
PCT/IB/308 Form for PCT/EP2011/059523.
English language abstract for FR 2 679 771, (1993).

* cited by examiner

*Primary Examiner* — Eisa Elhilo
(74) *Attorney, Agent, or Firm* — O'Brien Jones, PLLC

(57) ABSTRACT

The invention relates to a composition for dyeing keratin fibers, and in particular human keratin fibers such as the hair, comprising at least one 2-pyrrolidone functionalized in the 4 position with a carboxylic acid or amide radical, and at least one hydrophobic direct dye or a pigment; a dyeing process using this composition. Similarly, the invention relates to the use of the said pyrrolidone combined with a direct dye or a pigment for dyeing keratin fibers, and especially to the use of the said pyrrolidone for improving the color uptake onto the fibers of direct dyes that are sparingly soluble or insoluble in aqueous-alcoholic supports. The invention also relates to novel pyrrolidone derivatives. The present invention makes it possible in particular to obtain direct dyeing on keratin fibers that is fast, resistant to washing, chromatic and powerful.

17 Claims, No Drawings

COMPOSITION COMPRISING AT LEAST ONE 2-PYRROLIDONE FUNCTIONALIZED IN THE 4 POSITION WITH A CARBOXYLIC ACID OR AMIDE, AND AT LEAST ONE DIRECT DYE OR A PIGMENT FOR DYEING KERATIN FIBRES

This is a national stage application of PCT/EP2011/059523, filed internationally on Jun. 8, 2011, which claims the benefit of U.S. Provisional Application No. 61/357,650, filed on Jun. 23, 2010, and claims priority to French Application No. 1054557, filed Jun. 9, 2010.

The invention relates to a composition for dyeing keratin materials, and in particular human keratin fibres such as the hair, comprising at least one 2-pyrrolidone functionalized in the 4 position with an acid or amide radical, and at least one pigment and/or hydrophobic direct dye; a dyeing process using this composition. The invention also relates to novel pyrrolidone derivatives.

It is known practice to dye keratin fibres, especially human keratin fibres, by direct dyeing. The process conventionally used in direct dyeing consists in applying to the keratin fibres "direct" dyes, which are coloured and colouring molecules that have affinity for the said fibres. Generally, these dyes are predissolved in aqueous-alcoholic formulation supports. The compositions comprising these dyes are then left to stand on the fibres so that they diffuse therein, and the fibres are then rinsed.

The colorations resulting therefrom are temporary or semi-permanent colorations since they have a tendency to fade out rapidly after successive washing with shampoo. Specifically, most of the dyes used in direct dyeing are water-soluble and are desorbed from the fibre during shampooing.

It has moreover already been proposed to use pigments, as in patent application FR 2 741 530, which recommends the use, for the dyeing of keratin fibres, of a composition comprising particular film-forming polymers and dispersed pigments. The colorations obtained via this dyeing method have the drawback of having poor shampoo fastness and of giving unsatisfactory colorations especially in terms of chromaticity.

2-Pyrrolidone derivatives functionalized with a carboxylic acid function in the 4 position are known in the field of inks (see, for example, EP 1 342 759 and WO 2008/131 396); for improving the transdermal passage of medicaments (*Int. J. Pharmaceutics,* 44 (1-3), 15-24 (1988)) and as natural gas inhibitors (EP 2 028 247 and EP 2 022 781). Other 2-pyrrolidones functionalized with amides have been used in inkjet printing formulations (EP 2 142 610); as antiepileptics (*J. Med. Chem.* 47(3), 530-549 (2004)); anticonvulsives (WO 2001/062 726) or as lubricant oil additives (FR 2 243 959) or gel additives (WO 2010/039 509).

In the field of dyeing keratin fibres, it is very difficult to use direct dyes or pigments that are sparingly soluble or insoluble in water or in aqueous-alcoholic solvents and to obtain satisfactory coloration of keratin fibres especially in terms of colour uptake, selectivity, power or chromaticity that can give rise to varied shades, while at the same time being sufficiently resistant to successive shampooing or to sweat.

This technical problem has been solved by treating human keratin materials using a process for dyeing keratin materials, by treating or applying to the keratin fibres:
i) at least one compound of formula (I); and
ii) at least one direct dye and/or at least one pigment that are sparingly soluble or insoluble in standard aqueous-alcoholic supports such as water, and in particular the pigment(s) and/or direct dye(s) have a solubility of less than 20 grams per liter of water; compound of formula (I):

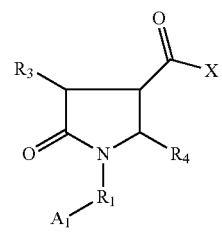

(I)

and also the organic or mineral acid or base salts thereof, optical isomers thereof: stereoisomers or enantiomers and diastereoisomers, geometrical isomers and tautomers thereof, and solvates thereof such as hydrates; in which formula (I):

X represents a hydroxyl group —OH or amino group —NH$_2$;

R$_1$ represents:
an optionally substituted hydrocarbon-based chain, the said chain is a saturated linear C$_1$-C$_{30}$ or branched C$_3$-C$_{30}$ or cyclic C$_3$-C$_7$ chain; the said hydrocarbon-based chain is optionally interrupted with:
i) one or more heteroatoms such as —O—, —N(R$_6$)— or —S—,
ii) one or more groups —S(O)—, —S(O)$_2$—, —C(O)—, —Nr$^+$(R$_6$)(R$_7$)—, or combinations of i) and ii), particularly —N(R$_6$)—C(O)—, —C(O)—N(R$_6$)—, —N(R$_6$)—C(O)—N(R$_7$)— or —S—S— and/or optionally
iii) a 3- to 6-membered saturated or unsaturated carbon-based ring optionally substituted with one or more identical or different radicals chosen especially from hydroxyl (OH) and amino (—NRR');
a divalent chain -Cycl-Alk-Cycl'- with:
Cycl and Cycl', which may be identical or different, preferentially identical, representing a cyclic hydrocarbon-based chain, particularly C$_5$-C$_6$ cycloalkylene, such as cyclohexylene or cyclopentylene and
Alk represents an optionally substituted (C$_1$-C$_6$)alkylene chain; preferentially unsubstituted;
an optionally substituted hydrocarbon-based chain, the said chain is a saturated linear C$_2$-C$_{30}$ or branched C$_3$-C$_{30}$ or cyclic C$_3$-C$_7$ chain; the said hydrocarbon-based chain is optionally interrupted with:
i) one or more heteroatoms such as —O—, —N(R$_6$)— or —S—,
ii) one or more groups —S(O)—, —S(O)$_2$—, —C(O)—, —N$^+$(R$_6$)(R$_7$)—, or combinations of i) and ii), particularly —N(R$_6$)—C(O)—, —C(O)—N(R$_6$)—, —N(R$_6$)—C(O)—N(R$_7$)— or —S—S— and/or optionally
iii) a 3- to 6-membered saturated or unsaturated carbon-based ring optionally substituted with one or more identical or different radicals chosen especially from hydroxyl (OH) and amino (—NRR');

$R_1$ may also be substituted with one or more radicals (E), preferentially a single radical (E):

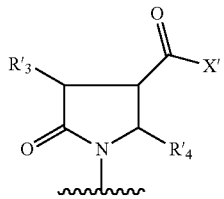
(E)

in which formula (E):

X' represents a hydroxyl group —OH or amino group —NH$_2$;

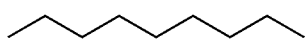

representing the point of attachment of the radical (E) to the rest of the molecule;

$A_1$, represents: a hydrogen atom or a group chosen from a) —OH; b) —SH; c) —NRR'; d) —O—P(O)(OH)$_2$; e) —O—S(O)$_2$OH; f) —S(O)$_2$OH; g) —C(O)OH; h) saturated or unsaturated 3- to 6-membered (hetero)cycle optionally substituted with one or more identical or different radicals chosen from (hydroxy)(C$_1$-C$_6$)alkyl, hydroxyl and —NRR', the said (hetero)cycle possibly being cationic; i) —N$^+$(R$_7$)(R$_8$)(R$_9$); j) RR'N—C(=NR'')—N(R)—; particularly

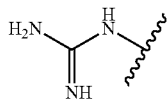

and; k) a radical of formula (G)

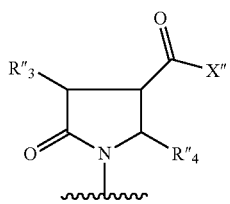
(G)

in which formula (G) X'' represents a hydroxyl group —OH or amino group —NH$_2$;

$R_3$, $R_4$, $R'_3$, $R'_4$, $R''_3$ and $R''_4$, which may be identical or different, represent a hydrogen atom or a linear $C_1$-$C_{12}$ or branched $C_3$-$C_{12}$ alkyl chain;

$R_6$ represents a hydrogen atom or a linear ($C_1$-$C_{20}$)alkyl or branched ($C_3$-$C_{20}$)alkyl group, optionally substituted with a radical (G);

$R_7$, $R_8$ and $R_9$, which may be identical or different, representing a hydrogen atom or a group ($C_1$-$C_6$)alkyl optionally substituted with one or more hydroxyl groups;

R, R' and R'', which may be identical or different, represent a hydrogen atom or a group ($C_1$-$C_{18}$)alkyl optionally substituted with one or more hydroxyl groups;

it being understood that when $A_1$ and/or $R_1$ contain or denote a cationic group, the electrical neutrality of the compounds of formula (I) is ensured by an anionic counterion or a mixture of anionic counterions such as cosmetically acceptable organic or mineral anions, particularly acetate, lactate, tartrate, citrate, halide (Cl$^-$, Br$^-$), SO$_4^{2-}$, MeSO$_4^-$, EtSO$_4^-$, ethosulfate, hydrogen sulfate, para-toluenesulfonate, mesylate.

Another subject of the invention is novel derivatives of formula (I) chosen from compounds 1 to 12, 14, 17, and 19 a 24 of the following formula formulae:

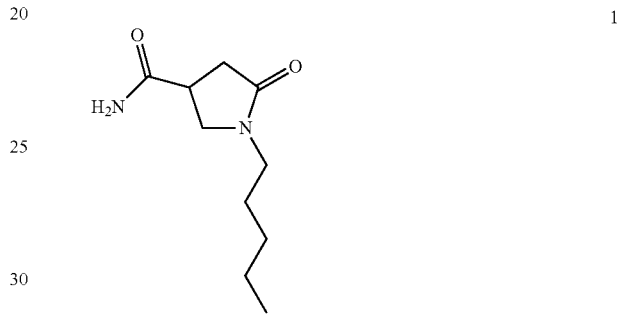
1

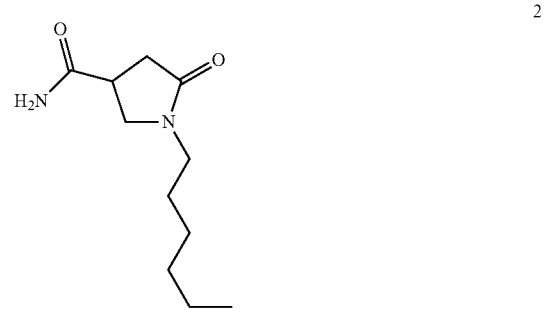
2

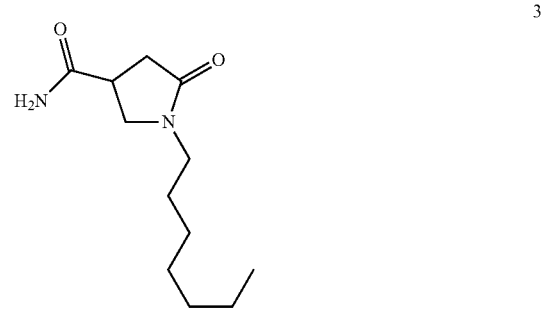
3

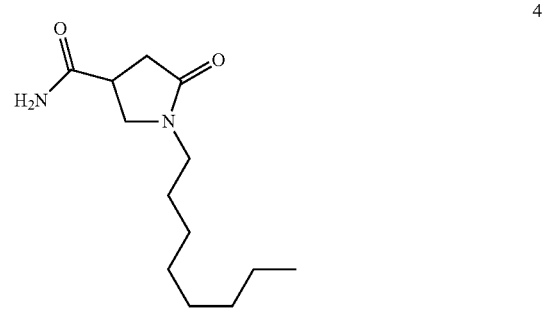
4

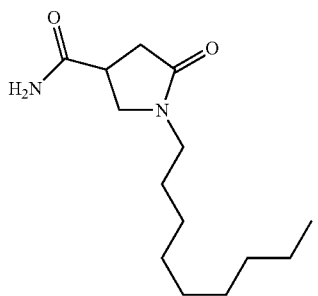
5
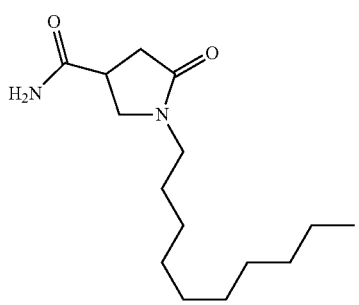
6
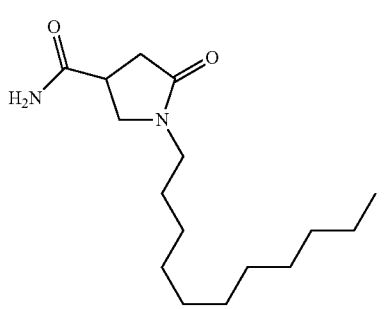
7
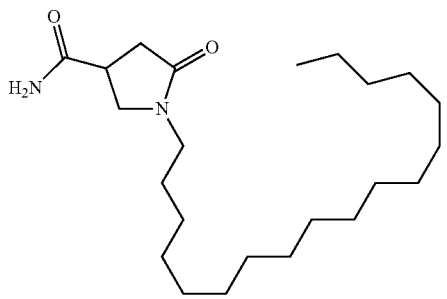
8
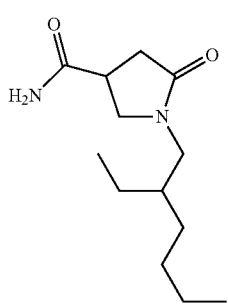
9
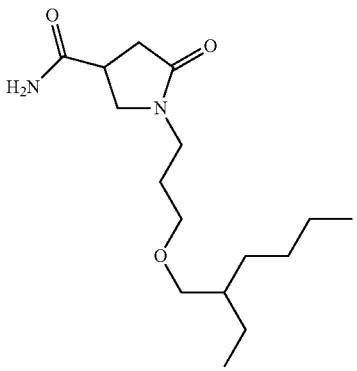
10
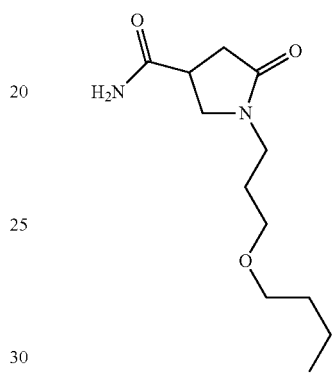
11
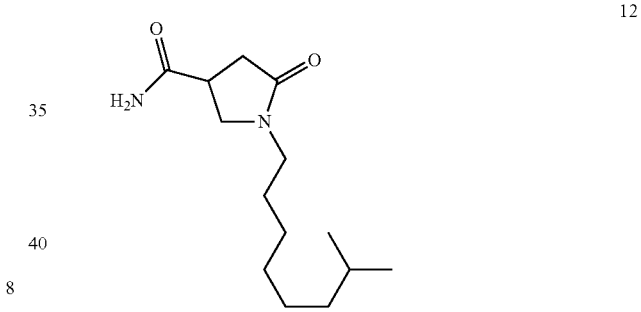
12
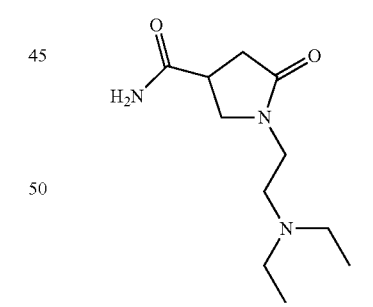
13
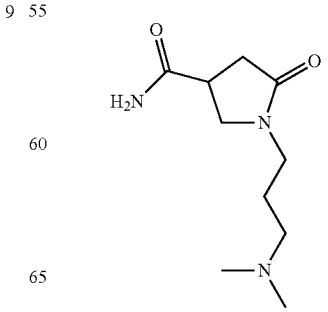
14

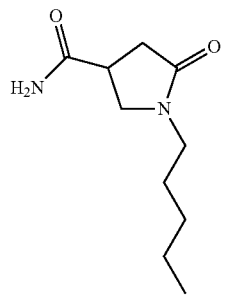

15

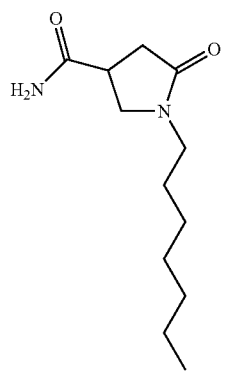

16

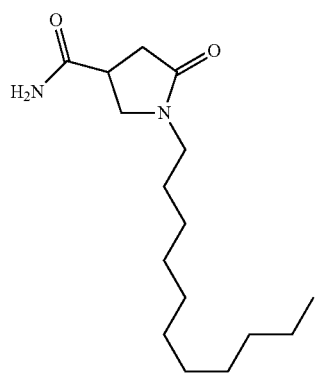

17

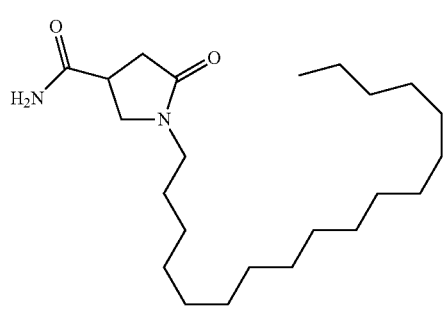

18

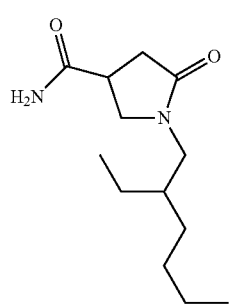

19

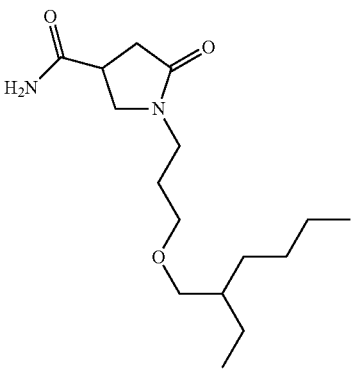

20

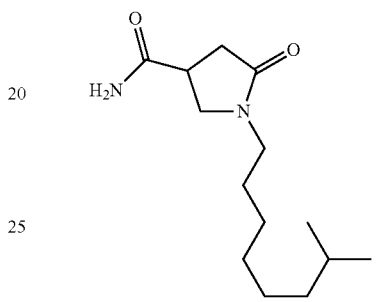

21

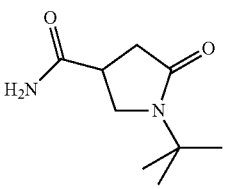

22

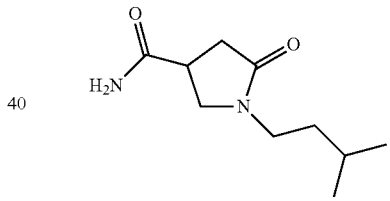

23

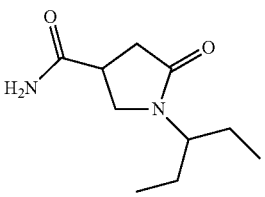

24

Compounds 1 to 24, and also the organic or mineral acid or base salts thereof, optical isomers and enantiomers thereof, and solvates thereof such as hydrates.

Another subject of the invention is a Composition comprising, in a suitable cosmetic medium:
  i) one or more compounds of formula (I); and
  ii) one or more pigments and/or one or more direct dyes that are sparingly soluble or insoluble in standard aqueous-alcoholic supports such as water, and in particular the pigment(s) and/or direct dye(s) have a solubility of less than 20 grams per liter of water;
with the proviso that the compound of formula (I) in the composition of the invention is other than (a) or (b) when the direct dye or pigment is of black dye type

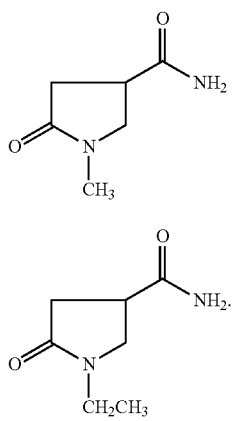

(a)

(b)

Similarly, a subject of the invention is the use of the said pyrrolidone of formula (I) combined with a pigment and/or a direct dye that are sparingly soluble or insoluble in aqueous-alcoholic supports for dyeing keratin materials, especially the use of the said pyrrolidone for improving the colour uptake on keratin fibres of the said pigments and direct dyes that are sparingly soluble or insoluble in aqueous-alcoholic supports.

The use of the composition and the process according to the invention, as defined previously, makes it possible to overcome the drawbacks, especially in terms of solubility, colour uptake, selectivity, power or chromaticity, while at the same time being particularly resistant to successive shampooing or to sweat.

For the purposes of the present invention, and unless otherwise indicated:

- the "saturated carbon-based rings" are cycloalkyls such as cyclopropyl, cyclobutyl, cyclopentyl and cyclohexyl; preferentially cyclohexyl;
- the "unsaturated carbon-based rings" are $C_3$-$C_6$ rings comprising from 1 to 3 conjugated or unconjugated double bonds, particularly of cycloalkylene type such as hexylenyl, or aryl such as phenyl;
- the "heterocycles" are hydrocarbon-based rings in which one or more of the carbon atoms have been substituted with one or more heteroatoms such as an oxygen, sulfur or nitrogen atom, the said heterocycle may be saturated; they are heterocycloalkyls that are preferentially 3- to 6-membered such as morpholinyl, thiomorpholinyl, piperidyl, piperazinyl, pyrrolidinyl, tetrahydrofuryl or azepanyl, preferentially pyrrolidinyl and morpholinyl;
- or alternatively the said heterocycle is unsaturated and comprises from 1 to 3 conjugated or unconjugated double bonds, particularly of heterocycloalkenyl or heteroaryl type as defined below
- an "aryl" radical represents a fused or non-fused monocyclic or polycyclic group containing from 6 to 22 carbon atoms, and in which at least one ring is aromatic; preferentially, the aryl radical is a phenyl, biphenyl, naphthyl, indenyl, anthracenyl or tetrahydronaphthyl;
- a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof;
- the "(hetero)cycles" are either heterocycles or saturated or unsaturated carbon-based rings as defined previously;
- the "cyclic hydrocarbon-based chain" is a divalent 3- to 7-membered chain, which may be saturated or unsaturated with 1 to 3 unsaturations, especially such as cycloalkylene or arylene such as those chosen from:

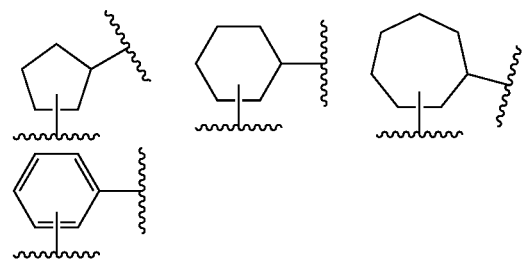

the aromatic part of a (hetero)cyclic radical may be substituted with a substituent borne by a carbon atom, chosen from:

- a $C_1$-$C_{16}$ and preferably $C_1$-$C_8$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another heteroatom identical to or different from nitrogen;
- a halogen atom such as chlorine, fluorine or bromine; a hydroxyl group;
- a $C_1$-$C_2$ alkoxy radical;
- a $C_2$-$C_4$ (poly)hydroxyalkoxy radical;
- an amino radical;
- nitro;
- a 5- or 6-membered heterocycloalkyl radical;
- an optionally cationic 5- or 6-membered heteroaryl radical, preferentially imidazolium, optionally substituted with a ($C_1$-$C_4$)alkyl radical, preferentially methyl;
- an amino radical substituted with one or two identical or different $C_1$-$C_6$ alkyl radicals, optionally bearing at least:
  i) a hydroxyl group,
  ii) an amino group optionally substituted with one or two optionally substituted $C_1$-$C_3$ alkyl radicals, the said alkyl radicals possibly forming with the nitrogen atom to which they are attached a saturated or unsaturated, optionally substituted 5- to 7-membered heterocycle, optionally comprising at least one other heteroatom identical to or different from nitrogen, iii) a quaternary ammonium group —N⁺R'R"R'", M⁻ for which R', R" and R'", which may be identical or different, represent a hydrogen atom, or a $C_1$-$C_4$ alkyl group; and M represents the organic or mineral counterion such as halide, iv) an optionally cationic 5- or 6-membered heteroaryl radical, preferentially imidazolium, optionally substituted with a ($C_1$-$C_4$)alkyl radical, preferentially methyl;

an acylamino radical (—NR—C(O)R') in which the radical R is a hydrogen atom or a $C_1$-$C_4$ alkyl radical optionally bearing at least one hydroxyl group and the radical R' is a $C_1$-$C_2$ alkyl radical;

a carbamoyl radical ((R)$_2$N—C(O)—) in which the radicals R, which may be identical or different, represent a hydrogen atom or a $C_1$-$C_4$ alkyl radical optionally bearing at least one hydroxyl group;

a carboxylic acid or ester radical, (—O—C(O)R') or (—C(O)OR'), in which the radical R' is a hydrogen atom or a $C_1$-$C_4$ alkyl radical optionally bearing at least one hydroxyl group, and the radical R' is a $C_1$-$C_2$ alkyl radical;

the carboxylic radical possibly being in acid or salified form (preferably with an alkali metal or a substituted or unsubstituted ammonium);

an alkylsulfonylamino radical (R'S(O)$_2$—NR—) in which the radical R represents a hydrogen atom or a $C_1$-$C_4$ alkyl radical optionally bearing at least one hydroxyl group and the radical R' represents a $C_1$-$C_4$ alkyl radical or a phenyl radical;

an aminosulfonyl radical ((R)$_2$N—S(O)$_2$—) in which the radicals R, which may be identical or different, represent a hydrogen atom or a $C_1$-$C_4$ alkyl radical optionally bearing at least one hydroxyl group;

a cyano group (CN);

a polyhaloalkyl group, preferentially trifluoromethyl ($CF_3$);

the non-aromatic part of a cyclic or heterocyclic radical may be substituted with at least one substituent borne by a carbon atom, chosen from the groups:

hydroxyl, $C_1$-$C_4$ alkoxy, $C_2$-$C_4$ (poly)hydroxyalkoxy, alkylcarbonylamino (RC(O)—NR'—) in which the radical R' is a hydrogen atom or a $C_1$-$C_4$ alkyl radical optionally bearing at least one hydroxyl group, and the radical R is a $C_1$-$C_2$ alkyl radical or an amino radical substituted with two $C_1$-$C_4$ alkyl groups, which may be identical or different, optionally bearing at least one hydroxyl group, the said alkyl radicals possibly forming with the nitrogen atom to which they are attached a saturated or unsaturated, optionally substituted 5- to 7-membered heterocycle optionally comprising at least one other heteroatom identical to or different from nitrogen;

alkylcarbonyloxy (RC(O)—O—) in which the radical R is a $C_1$-$C_4$ alkyl radical or an amino radical substituted with one or two identical or different $C_1$-$C_4$ alkyl groups optionally bearing at least one hydroxyl group, the said alkyl radicals possibly forming with the nitrogen atom to which they are attached a saturated or unsaturated, optionally substituted 5- to 7-membered heterocycle, optionally comprising at least one other heteroatom identical to or different from nitrogen;

alkoxycarbonyloxy (RO—C(O)—) in which the radical R is a $C_1$-$C_4$ alkyl radical or an amino radical substituted with one or two identical or different $C_1$-$C_4$ alkyl groups optionally bearing at least one hydroxyl group, the said alkyl radicals possibly forming with the nitrogen atom to which they are attached a saturated or unsaturated, optionally substituted 5- to 7-membered heterocycle, optionally comprising at least one other heteroatom identical to or different from nitrogen;

a compound containing one or more cationic groups, it being understood that the said compound comprises at least one cationic group other than an acid salt, the said compound particularly comprising at least one group chosen from tri($C_1$-$C_6$)alkylammonium, guanidinium —N⁺($R_6$)($R_7$)—; cationic (hetero)cycle or heteroaryl; —N⁺($R_6$)($R_7$)($R_8$) as defined previously or —N⁺R'R"R'" as defined below;

a cyclic or heterocyclic radical, or a non-aromatic portion of an aryl or heteroaryl radical, may also be substituted with one or more oxo groups;

a hydrocarbon-based chain is unsaturated when it comprises one or more double bonds and/or one or more triple bonds which may be conjugated or unconjugated; preferentially, it comprises from 1 to 3 double bonds;

a "salt of an organic or mineral acid" is chosen, for example, from a solvent derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid P(O)(OH)$_3$; xiii) acetic acid $CH_3C(O)OH$; xiv) triflic acid $CF_3S(O)_2OH$; and xv) tetrafluoroboric acid $HBF_4$;

a "salt of an organic or mineral base" is chosen, for example, from a salt derived from mineral bases such as: i) sodium hydroxide NaOH, ii) potassium hydroxide KOH, or from organic bases such as iii) aqueous ammonia; iv) amines and hydroxyamines such as (tri)($C_1$-$C_6$) alkylamine, (tri)hydroxy($C_1$-$C_6$)alkylamine, and also salts derived from alkali metals and alkaline-earth metals;

an "anionic counterion" is an anion or an anionic group associated with the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O⁻ such as methanesulfonate or mesylate, and ethanesulfonate; iv) arylsulfonates: Ar—S(O)$_2$O⁻ such as benzenesulfonate and toluenesulfonate or tosylate; v) citrate; vi) succinate; vii) tartrate; viii) lactate; ix) alkyl sulfates: Alk-O—S(O)O⁻ such as methyl sulfate and ethyl sulfate; x) aryl sulfates: Ar—O—S(O)O⁻ such as benzene sulfate and toluene sulfate; xi) alkoxy sulfates: Alk-O—S(O)$_2$O— such as methoxy sulfate and ethoxy sulfate; xii) aryloxy sulfates: Ar—O—S(O)$_2$O⁻; xiii) phosphate; xiv) acetate; xv) triflate; and xvi) borates such as a tetrafluoroborate;

an "alkyl" radical is a saturated, linear or branched hydrocarbon-based radical, containing from 1 to 6 carbon atoms and particularly from 1 to 3 carbon atoms, such as the methyl or ethyl radical;

an "alkoxy" radical is an "alkyl-oxy" alkyl-O— radical in which the alkyl part is as defined previously;

the alkyl, alkoxy or (hetero)cycloalkyl radicals followed by "optionally substituted with . . . " means that the said radicals may have one or more hydrogen atoms replaced with one or more substituents in question, particularly one or two substituents in question;

the expression "optionally substituted" attributed to the alkyl radical or to the hydrocarbon-based chain means that the said alkyl radicals or hydrocarbon-based chain may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, the said alkyl radicals possibly forming with the nitrogen atom that bears them a 5- to 7-membered heterocycle, optionally comprising another heteroatom identical to or different from nitrogen; v) or a quaternary ammonium group —N⁺R'R"R'", M⁻ for which R', R" and R'", which may be identical or different, represent a hydrogen atom or a $C_1$-$C_4$ alkyl group, or else —N⁺R'R"R'", forms a heterocycle of heteroaryl type such as imidazolium optionally substituted with a $C_1$-$C_4$ alkyl group, and M⁻ represents the counterion of the organic or mineral acid or of the corresponding halide; vi) or a quaternary ammonium group —N⁺($R_6$)($R_7$)($R_8$) as defined previously.

Compounds of formulae (I) and (I')

According to one particular embodiment of the invention, the compounds of formula (I) are such that X, X' and X" represent a hydroxyl group. Another advantageous variant of the invention is when the compounds of formula (I) contain radicals X, X' and X" that represent an amino group $NH_2$.

According to another particular embodiment of the invention, in the compounds of formula (I), the radicals $R_3$, $R_4$, $R'_3$, $R'_4$, $R''_3$ and $R''_4$ represent a hydrogen atom.

A particularly advantageous variant of the invention concerns the compounds of formula (I) in which $R_1$ denotes a saturated linear $C_1$-$C_{20}$ or branched $C_3$-$C_{20}$ hydrocarbon-based chain optionally interrupted with one or more heteroatoms such as O, S or groups —N($R_6$)—, N⁺($R_6$)($R_7$)—, —N($R_6$)—C(O)—, —C(O)—N($R_6$)—, —N($R_6$)—C(O)—N($R_7$)— or —S—S— and/or optionally substituted with one or more identical or different radicals chosen from hydroxyl (OH) and —NRR'.

More particularly, $R_1$ represents a saturated $C_1$-$C_{10}$ hydrocarbon-based chain optionally interrupted with one (or more) oxygen atoms.

According to one particular mode of the invention, $R_1$ represents a saturated hydrocarbon-based chain interrupted with several oxygens, such that the said chain is: —[O—$CH_2$—$CH_2$]$_n$—O—, with n representing an integer between 1 and 4 inclusive.

According to another advantageous variant of the invention, the compound of formula (I) is such that the radical $R_6$ represents a group ($C_1$-$C_6$)alkyl optionally substituted with a radical (G) as defined previously; and $R_7$ represents a hydrogen atom or a group ($C_1$-$C_6$)alkyl.

Preferentially, the compound of formula (I) is such that:
$A_1$ represents:
a hydrogen atom,
a radical —OH,
a radical —S(O)$_2$OH,
a radical NRR',
a radical —O—P(O)OH$_2$,
a radical —O—S(O)$_2$OH,
a radical —C(O)OH, a saturated or unsaturated 4- to 6-membered (hetero)cycle, this (hetero)cycle possibly being cationic,
a radical of formula: —N⁺($R_6$)($R_7$)($R_8$) or (G).

According to one preferred mode of the invention, the compound of formula (I) contains only one 2-pyrrolidinone unit functionalized in position 4 with a carboxylic acid or amide, i.e. not containing any unit (E) or (G).

According to another preferred mode of the invention, the compound of formula (I) contains two or three 2-pyrrolidinone units functionalized in position 4 with a carboxylic acid or amide of unit (E) and/or (G). More particularly, $R_1$ represents a divalent chain -alk-T-alk'- with
T representing:
either a covalent bond σ,
or a heteroatom such as O,
or a group —N(R)— with R representing a hydrogen atom or a group ($C_1$-$C_6$)alkyl or -alk"-(E);
or a divalent group —$X_a$-alk"-$X_b$— with $X_a$ and $X_b$, which may be identical or different, representing a heteroatom such as O or a group NH;
alk, alk' and alk", which may be identical or different, representing a group ($C_1$-$C_6$)alkylene, preferentially alk, alk' and alk" are identical and represent an ethylene or propylene chain;
$A_1$ represents a radical (G) as defined previously.

According to one preferred variant of the invention, the compound of formula (I) contains $R_7$, $R_8$ and $R_9$, which denote, independently of each other, a group ($C_1$-$C_4$)alkyl.

More particularly, the compounds of formula (I) are chosen from those comprising two or three pyrrolidone radicals of formula (I'):

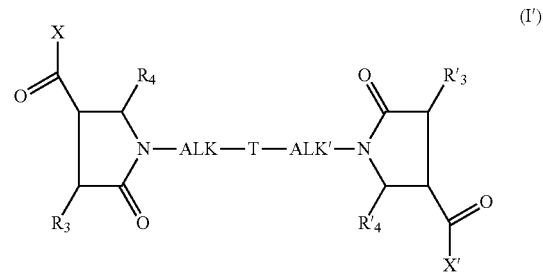

in which formula (I'):
T represents:
either a covalent bond σ,
or a heteroatom such as O,
or a group —N(R)— with R representing a hydrogen atom or a group ($C_1$-$C_6$)alkyl or -alk"-(G);
or a divalent group —$X_a$-alk"-$X_b$— with $X_a$ and $X_b$, which may be identical or different, representing a heteroatom such as O or a group NH;
alk, alk' and alk", which may be identical or different, representing a group ($C_1$-$C_6$)alkylene, preferentially alk, alk' and alk" are identical and represent an ethylene or propylene chain; and
(G), X, X', $R_3$, $R'_3$, $R_4$ and $R'_4$ are as defined previously; preferentially, the compound of formula (I') is symmetrical, and contains an axis of symmetry at C2 or at C3.

According to one particularly advantageous embodiment of the invention, the compounds of formula (I) are such that X=OH, $R_3$ and $R_4$ and $A_1$ represent a hydrogen atom; and $R_1$ represents a linear $C_1$-$C_8$ or branched $C_3$-$C_8$ alkylene group; corresponding to the formula:

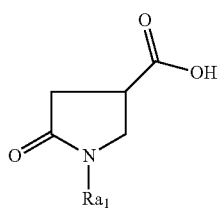
with Ra₁ representing a linear $C_1$-$C_8$ or branched $C_3$-$C_8$ alkyl group.
Preferentially, the compounds of formulae (I) and (I') of the invention are chosen from those of the following list:
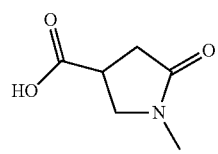
a
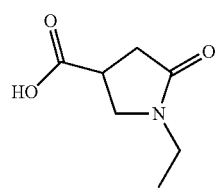
b
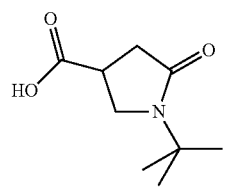
c
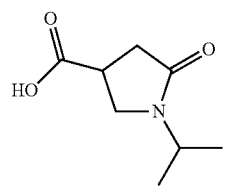
d
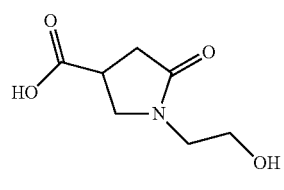
e
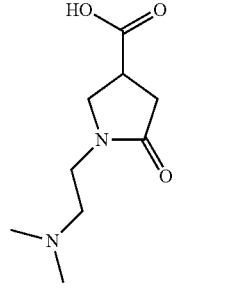
f
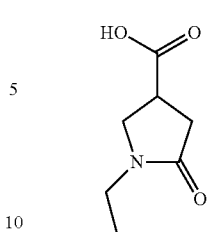
g
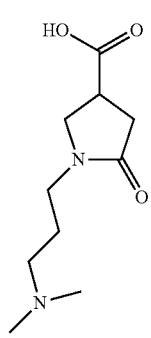
h
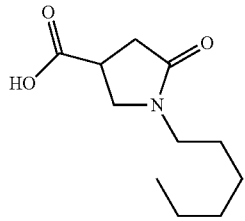
i
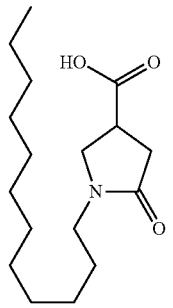
j
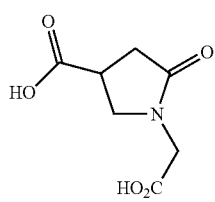
k
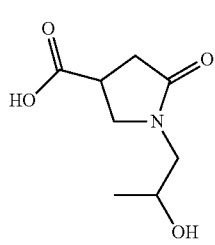
l

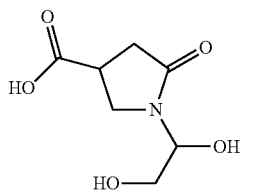
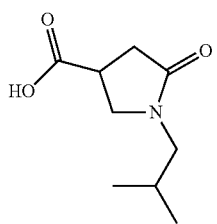
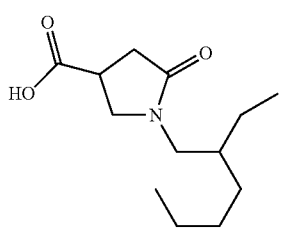
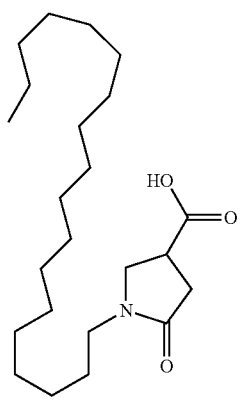
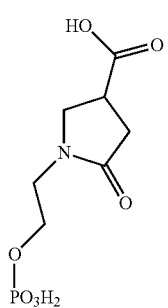
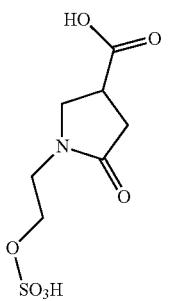
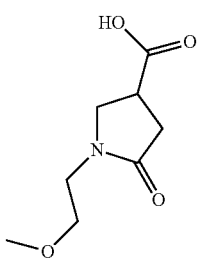
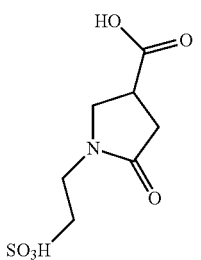
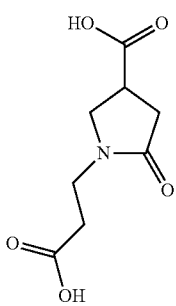
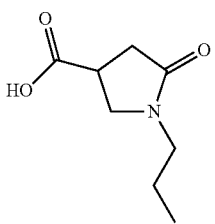

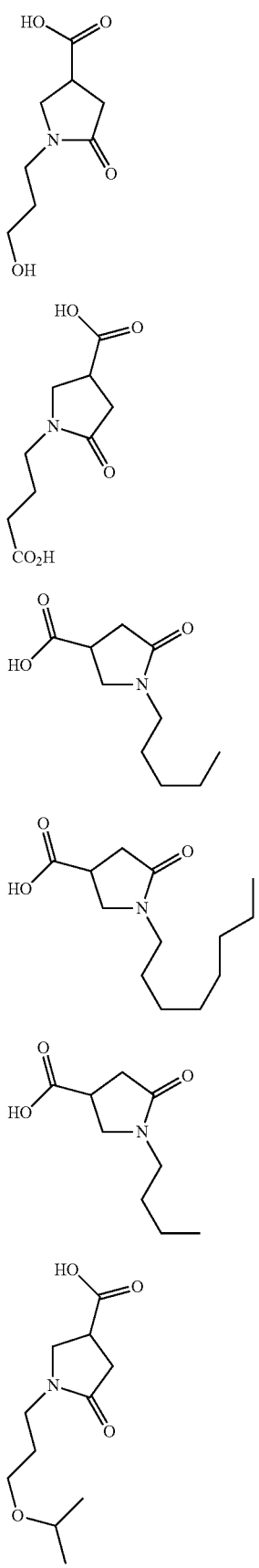
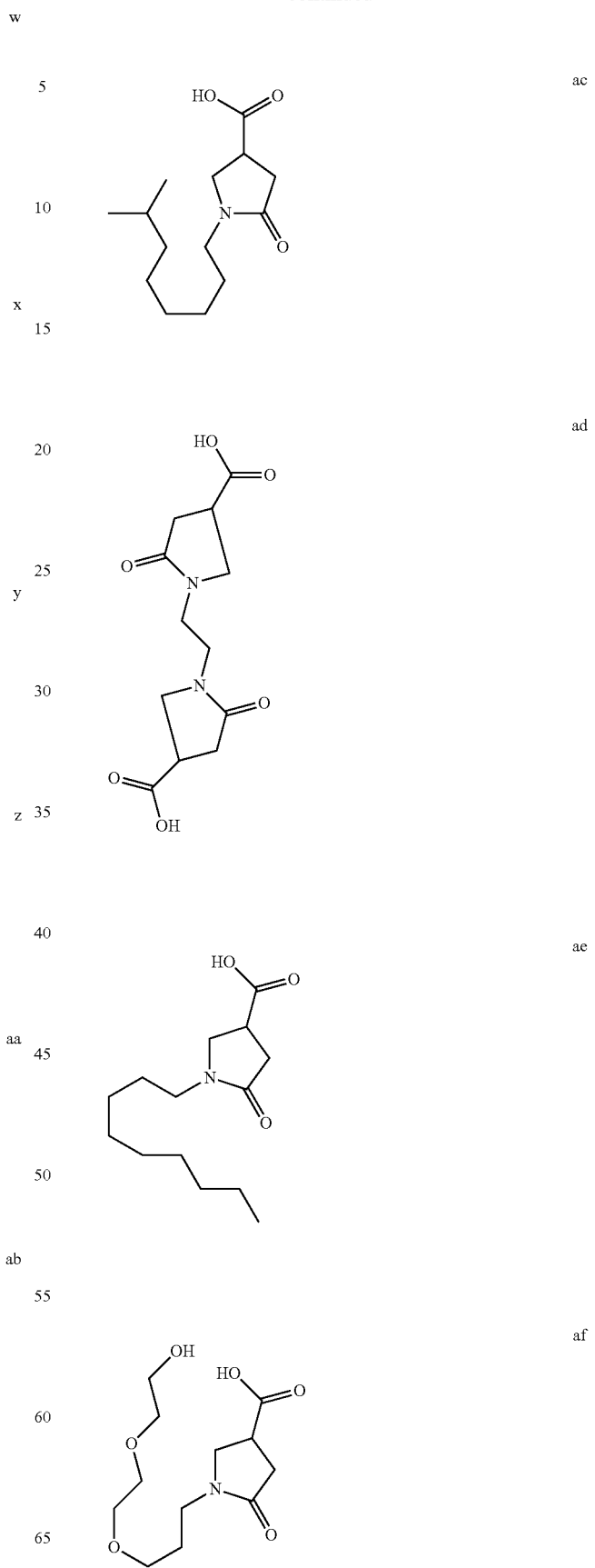

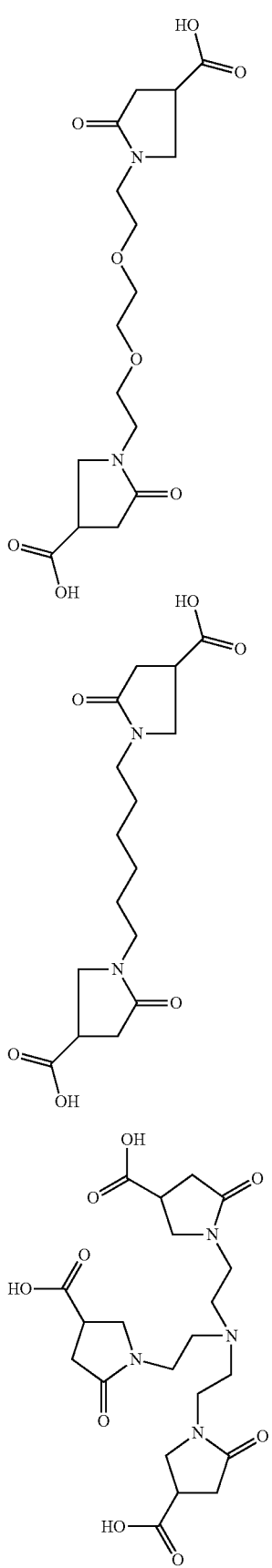
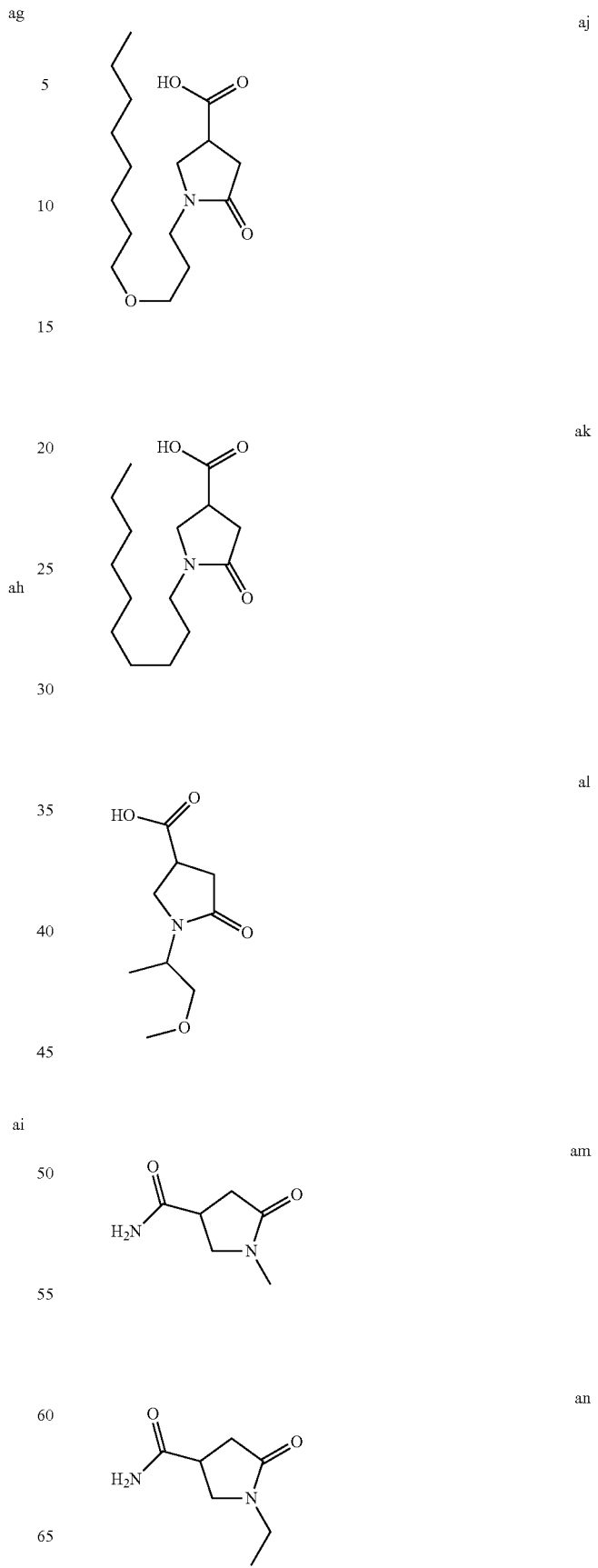

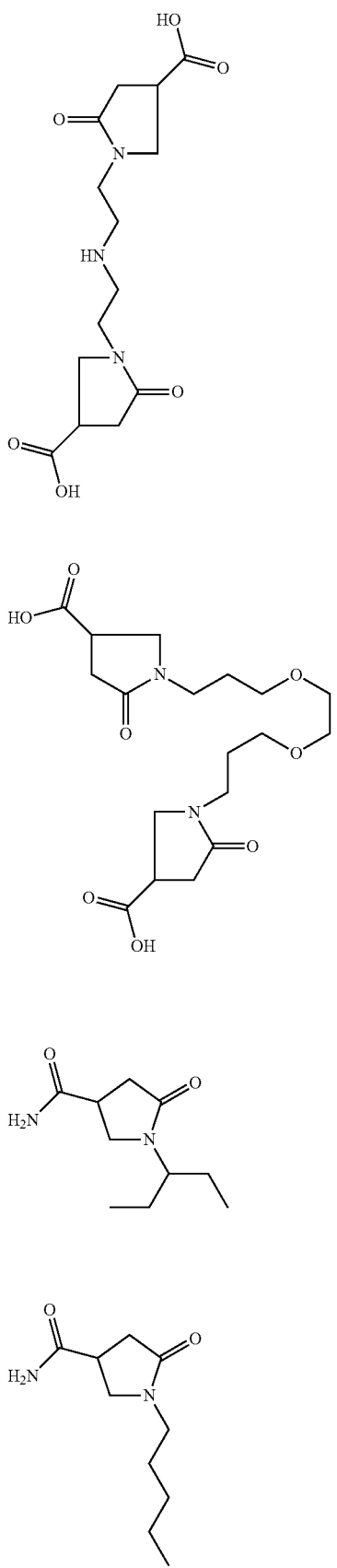
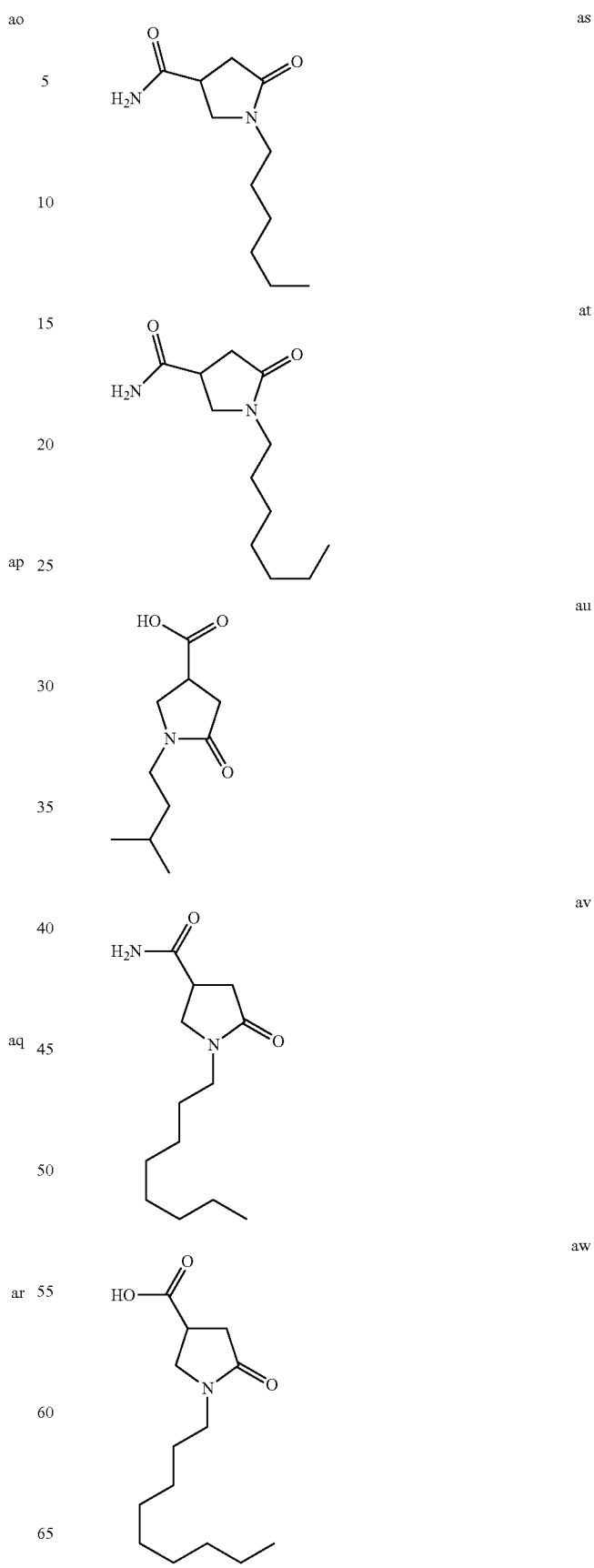

25
-continued
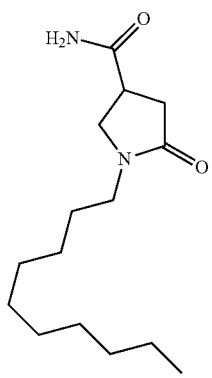
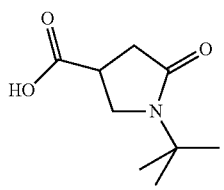
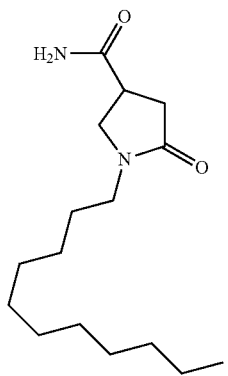
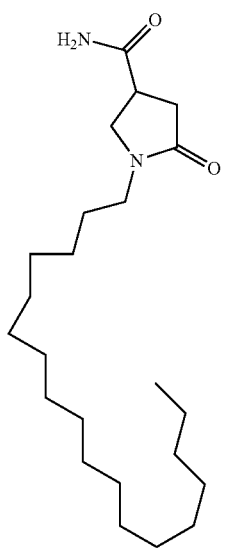
26
-continued
ax
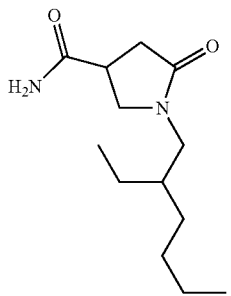
ay
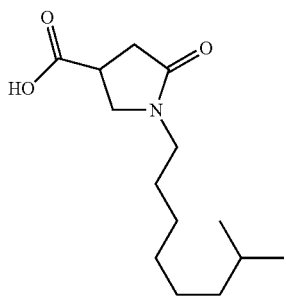
az
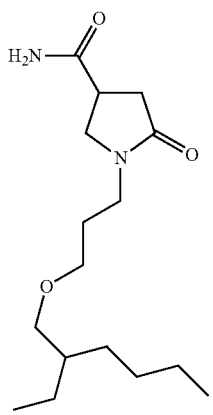
ba
bb
bc
bd
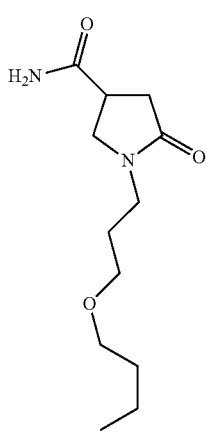
be

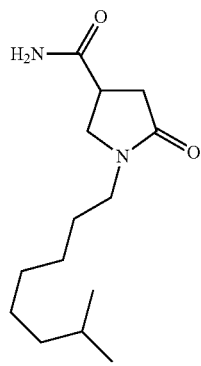
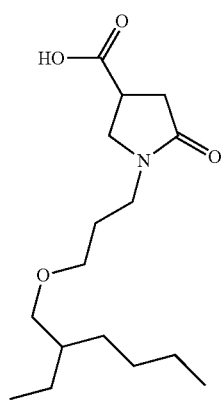
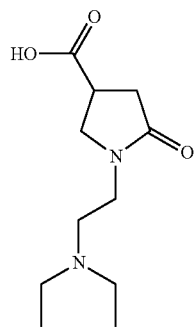
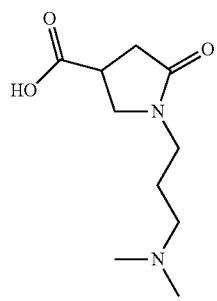
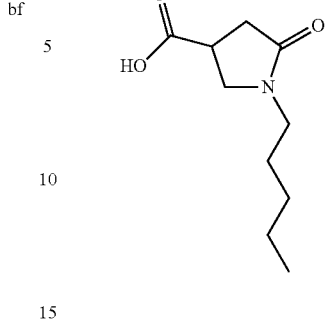
bf
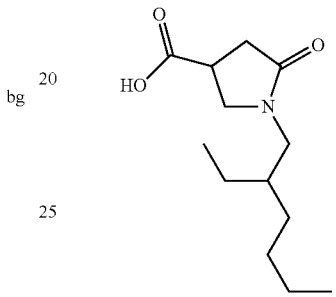
bg
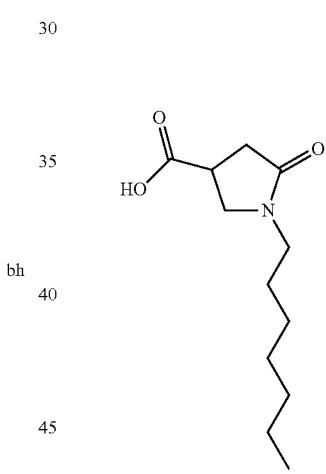
bl
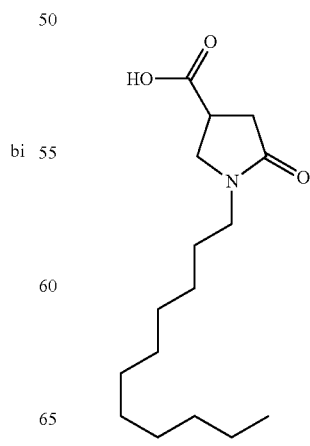
bn

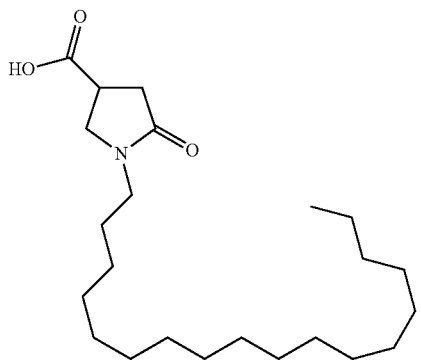

Compounds a to bo, and also the organic or mineral acid or base salts thereof, optical isomers thereof; stereoisomers or enantiomers and diastereoisomers thereof, and solvates thereof such as hydrates.

Preferentially, the compounds of formula (I') as defined previously are chosen from ag, ah, ai and ao.

The synthesis of the derivatives of formula (I) in which the radical X represents a hydroxyl group and $R_3$ and $R_4$=H is described in the following articles: *Journal of Medicinal Chemistry* 30(10), 1711-15 (1987) and *Journal of Medicinal Chemistry* 49(21), 6308-6323 (2006)

These derivatives may be readily obtained from itaconic acid of formula (IV) by condensation with the primary amine of formula (III) in the presence or absence of a solvent to give (I) according to the following scheme, it being understood that the starting reagents (III) and (IV) are readily available via the standard synthetic routes known to those skilled in the art or alternatively are commercially available:

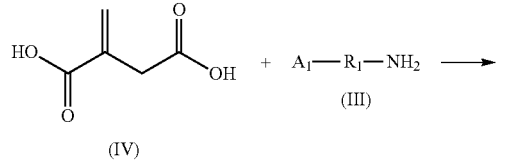

The derivatives of formula (I) in which the radical X represents an amino group and $R_3$ and $R_4$=H may be readily obtained:
either by transformation of the acid obtained previously into an amide, inspired by what is described in patent application US 2005/065 204, Zhongguo Yiyao Gongye Zazhi, 37(6) 375-376, or in international patent application WO 2007/140 982:

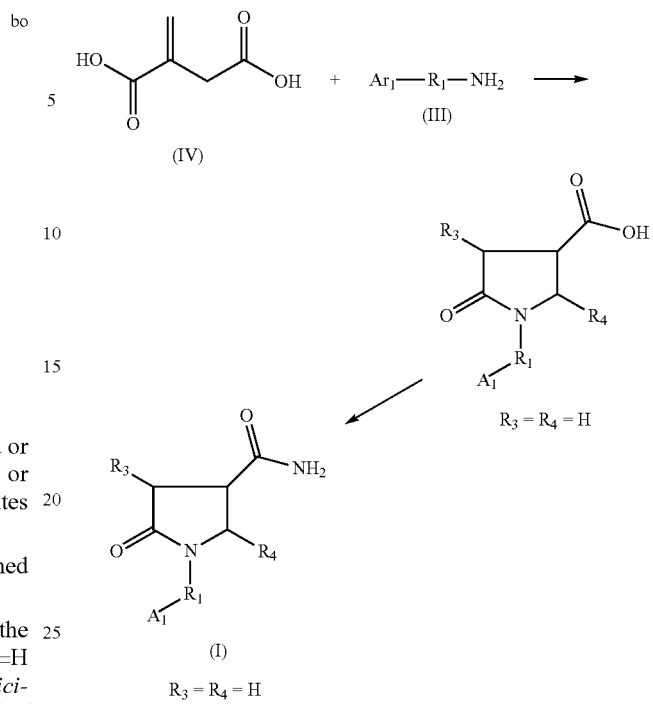

or in two steps via condensation of a diester of itaconic acid of formula (II) with a primary amine of formula (III), followed by transformation of the ester to an amide, inspired by what is described in *Journal of Medicinal Chemistry*, 47(3) 530-545 2004:

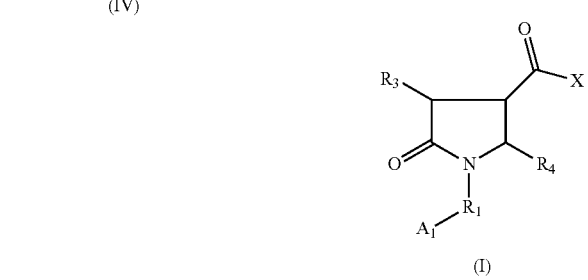

Pigments and Direct Dyes that are Sparingly Soluble or Insoluble in Aqueous-Alcoholic Supports The other ingredient combined with the compound of formula (I) or (I') in the invention is a direct dye and/or pigment that is sparingly soluble or insoluble in standard aqueous-alcoholic supports.

Typically, the aqueous-alcoholic support comprises water and an alcohol. Preferentially, at least 50% water and at least 5% alcohol such as ethanol, denatured alcohol, propylene glycol, hexylene glycol, dipropylene glycol, benzyl alcohol or isopropyl alcohol.

According to one particularly preferred mode of the invention, the aqueous-alcoholic support contains only water.

The term "pigment" is intended to denote a white or coloured solid particle, which is naturally insoluble in the liquid hydrophilic and lipophilic phases usually used in cosmetics, or which is made insoluble by formulation in the form of a lake, where appropriate.

Pigments that may be mentioned include organic and inorganic pigments such as those defined and described in Ullmann's Encyclopedia of Industrial Chemistry "Pigment organics", 2005 Wiley-VCH Verlag GmbH & Co. KGaA, Weinheim 10.1002/14356007.a20 371 and ibid, "Pigments, Inorganic, 1. General" 2009 Wiley-VCH Verlag GmbH & Co. KGaA, Weinheim10.1002/14356007.a20_243.pub3

Azo pigments that contain one or more azo groups A-N=N—B with A representing an optionally substituted (hetero)aryl, B representing optionally substituted (hetero)aryl or —CH[C(O)—R]—C(O)—$X_1$-A', A' representing an optionally substituted (hetero)aryl and R representing a hydrogen atom or a group ($C_1$-$C_6$)alkyl, with the groups A, A' and B being (hetero)aryls that do not contain any solubilizing groups such as —$SO_3H$ or —COOH.

They may particularly be monoazo pigments including β-naphthols, monoazopyrrolones, benzimidazolone pigments; diazo pigments such as diazodiarylide pigments and bis(N-acetoacetarylide), and triazo or tetraazo pigments.

Mention may also be made of azo metal complex pigments.

Other pigments are also advantageous, namely isoindolinone and isoindoline pigments, phthalocyanin pigments; quinacridone pigments; perinone pigments; perylene pigments; anthraquinone pigments such as hydroxyanthraquinone pigments; aminoanthraquinone pigments including acylaminoanthraquinones and azo anthraquinone pigments; heterocyclic anthraquinones; polycarboxylic anthraquinone pigments, pyranthrone pigments; anthranthrone pigments; diketopyrrolopyrrole (DPP) pigments; thioindigo pigments; dioxazine pigments; triphenylmethane pigments; quinophthalone pigments; and fluorescent pigments.

When the dyes comprise one or more solubilizing groups such as —$SO_3H$ or —COOH, these dyes are made insoluble and consequently pigments by formation of a lake, i.e. by salification (e.g. Na, Ca, St, Ba, etc.) and divided mainly into β-naphthol and 2-hydroxy-3-naphthoic acid pigments "(BON) pigment lakes".

In the context of the present invention, the pigment may be at least partly organic.

According to one embodiment of the invention, the pigment is an organic pigment.

According to another embodiment of the invention, the pigment is a mineral pigment.

The microcapsules according to the invention comprise not more than 80% by weight of pigment relative to the weight of the polymer matrix. In particular, they may comprise from 0.5% to 75% by weight, for example from 1% to 70% by weight, especially from 20% to 65% by weight or even from 30% to 60% by weight of pigment relative to the weight of the polymer matrix.

Needless to say, the degree of encapsulation depends on the desired modification of the shade and may thus vary significantly according to the effect that it is desired to obtain.

As illustrations of pigments that may be used in the present invention, mention may be made of carbon black, titanium oxide, chromium oxide, pigments of D&C or FD&C type and lakes thereof, and especially those known under the names D&C Blue No. 4, D&C Brown No. 1, FD&C Green No. 3, D&C Green No. 5, D&C Green No. 6, FD&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, FD&C Red 40 lake, D&C Violet No. 2, Ext. D&C Violet No. 2, FD & C Blue No. 1, D&C Yellow No. 6, FD&C Yellow No. 6, D&C Yellow No. 7, Ext. D&C Yellow No. 7, D&C Yellow No. 8, D&C Yellow No. 10 or D&C Yellow No. 11, it being understood that when the said pigment is not naturally insoluble in the hydrophilic and lipophilic phases usually used in cosmetics, it is used in the form of a corresponding lake, as explained previously.

Examples of lakes that may especially be mentioned include lakes based on barium, strontium, calcium or aluminium, or alternatively diketopyrrolopyrroles.

As further examples of pigments that may be used in the present invention, mention may be made especially of mineral pigments, optionally surface-treated and/or coated, and especially titanium dioxide, zirconium oxide or cerium oxide, and also zinc oxide, iron oxide (black, yellow or red) or chromium oxide, manganese violet, ultramarine blue, chromium hydrate and ferric blue, or alternatively metal powders, for instance aluminium powder, copper powder, gold powder and silver powder.

Mention may also be made of pigments with an optical effect such as particles comprising a natural or synthetic organic or mineral substrate, for example glass, acrylic resins, polyester, polyurethane, polyethylene terephthalate, ceramics or aluminas, the said substrate being optionally covered with metal substances, for instance aluminium, gold, silver, platinum, copper or bronze, or with metal oxides, for instance titanium dioxide, iron oxide or chromium oxide.

They may also be nacres.

The term "nacres" should be understood as meaning iridescent particles, which are especially produced by certain molluscs in their shell, or alternatively which are synthesized.

The nacreous pigments may be chosen from mica coated with titanium or with bismuth oxychloride, titanium mica coated with iron oxides, titanium mica coated especially with ferric blue or with chromium oxide, titanium mica coated with an organic pigment of the abovementioned type, and also nacreous pigments based on bismuth oxychloride. Interference pigments, especially liquid-crystal or multilayer pigments, may also be used.

They may also be pigments having a structure that may be, for example, of sericite/brown iron oxide/titanium dioxide/silica type.

They may also be pigments having a structure that may be, for example, of silica microsphere type containing iron oxide.

As examples of pigments and lakes that are most particularly suitable for use in the present invention, mention may be made especially of D&C Red No. 7, titanium oxide, chromium oxide, lakes of the pigments of D&C and FD&C type mentioned above, and especially D&C Red No. 22 lake, Yellow No. 6 lake and FD&C Blue No. 1 lake.

These pigments may be in the form of powder or of pigmentary paste. They may be coated or uncoated.

The pigments in accordance with the invention may be chosen, for example, from white or coloured pigments, lakes, pigments with special effects such as nacres or flakes, and mixtures thereof.

Examples of white or coloured mineral pigments that may be mentioned include zirconium oxide or cerium oxide, chromium oxides, manganese violet, ultramarine blue, chromium hydrate and ferric blue.

Examples of white or coloured organic pigments that may be mentioned include nitroso, nitro, azo, xanthene, quinoline, anthraquinone and phthalocyanin compounds, compounds of metallic complex type, and isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005, the green pigments codified in the Color Index under the references CI 61565, 61570, 74260, the orange pigments codified in the Color Index under the references CI 11725, 15510, 45370, 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, 75470, the pigments obtained by oxidative polymerization of indole or phenolic derivatives as described in patent FR 2 679 771.

Pigmentary pastes of organic pigment may be used, such as the products sold by the company Hoechst under the name:
Jaune Cosmenyl 10G: Pigment Yellow 3 (CI 11710);
Jaune Cosmenyl G: Pigment Yellow 1 (CI 11680);
Orange Cosmenyl GR: Pigment Orange 43 (CI 71105);
Rouge Cosmenyl R: Pigment Red 4 (CI 12085);
Carmin Cosmenyl FB: Pigment Red 5 (CI 12490);
Violet Cosmenyl RL: Pigment Violet 23 (CI 51319);
Bleu Cosmenyl A2R: Pigment Blue 15.1 (CI 74160);
Vert Cosmenyl GG: Pigment Green 7 (CI 74260);
Noir Cosmenyl R: Pigment Black 7 (CI 77266).

The pigments in accordance with the invention may also be in the form of composite pigments as described in patent EP 1 184 426. These composite pigments may be compounds, especially particles, comprising:
an inorganic core,
at least one binder for fixing the organic pigments to the nucleus, and
at least one organic pigment at least partially covering the nucleus.

The term "lake" means dyes adsorbed onto insoluble particles, the assembly thus obtained remaining insoluble during use. The mineral substrates onto which the dyes are adsorbed are, for example, alumina, silica, calcium sodium borosilicate or calcium aluminium borosilicate, and aluminium. Among the organic dyes that may be mentioned is cochineal carmine.

Examples of lakes that may be mentioned include the products known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 O (CI 77 002), D & C Green 3 (CI 42 053), D & C Blue 1 (CI 42 090).

The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They are consequently in contrast with white or coloured pigments, which afford a standard opaque, semi-transparent or transparent uniform shade.

Examples of pigments with special effects that may be mentioned include white nacreous pigments such as mica coated with titanium or with bismuth oxychloride, coloured nacreous pigments such as mica coated with titanium and with iron oxides, mica coated with titanium and especially with ferric blue or with chromium oxide, mica coated with titanium and with an organic pigment as defined above, and also nacreous pigments based on bismuth oxychloride.

Mention may also be made of pigments with an interference effect not bound to a substrate, for instance liquid crystals (Helicones HC from Wacker), holographic interference flakes (Geometric Pigments or Spectra f/x from Spectratek). The pigments with special effects also comprise fluorescent pigments, whether they are substances that are fluorescent in daylight or that produce ultraviolet fluorescence, phosphorescent pigments, photochromic pigments, thermochromic pigments and quantum dots, for example sold by the company Quantum Dots Corporation.

Quantum dots are luminescent semiconductive nanoparticles capable of emitting, under light excitation, radiation with a wavelength of between 400 nm and 700 nm. These nanoparticles are known in the literature. In particular, they may be manufactured according to the processes described, for example, in U.S. Pat. No. 6,225,198 or U.S. Pat. No. 5,990,479, in the publications cited therein and also in the following publications: Dabboussi B. O. et al. "(CdSe)ZnS core-shell quantum dots: synthesis and characterization of a size series of highly luminescent nanocristallites" Journal of Physical Chemistry B, vol. 101, 1997, pp. 9463-9475 and Peng, Xiaogang et al., "Epitaxial Growth of highly Luminescent CdSe/CdS core/shell nanocrystals with photostability and electronic accessibility" Journal of the American Chemical Society, vol. 119, No. 30, pp. 7019-7029.

The pigments in accordance with the invention are preferably coloured pigments.

The variety of pigments used makes it possible to obtain a wide range of colours, and also particular optical effects such as metallic or interference effects.

The size of a pigment other than the nacres in solution is generally between 10 nm and 10 µm, preferably between 50 nm and 5 µm and even more preferentially between 100 nm and 3 µm. The size of a nacre in solution is generally between 1 and 200 µm, preferably between 1 and 80 µm and even more preferentially between 1 and 50 µm.

Among the mineral pigments, examples that may be mentioned include titanium dioxide (rutile or anatase) optionally surface-treated and codified in the Color Index under the reference CI 77891; black, yellow, red and brown iron oxides, codified under the references CI 77499, 77492 and 77491; manganese violet (CI 77742); ultramarine blue (CI 77007); hydrated chromium oxide (CI 77289); ferric blue (CI 77510).

Among the organic pigments that may be mentioned, for example, are the pigment Yellow 3 sold in particular under the trade name "Jaune Covanor W 1603" by the company Wackherr (CI 17710), "D & C Red No. 19" (CI 45170), "D & C Red No. 9" (CI 15585), "D & C Red No. 21" (CI 45380), "D & C Orange No. 4" (CI 15510), "D & C Orange No. 5" (CI 45370), "D & C Red No. 27" (CI 45410), "D & C Red No. 13" (CI 15630), "D & C Red No. 7" (CI 15850-1), "D & C Red No. 6" (CI 15850-2), "D & C Yellow No. 5" (CI 19140), "D & C Red No. 36" (CI 12085), "D & C Orange No. 10" (CI 45425), "D & C Yellow No. 6" (CI 15985), "D & C Red No. 30" (CI 73360), "D & C Red No. 3" (CI 45430), carbon black (CI 77266) and lakes based on cochineal carmine (CI 75470).

It is also possible to use nacreous pigments, which may be chosen in particular from white nacreous pigments such as mica coated with titanium oxide or bismuth oxide; coloured nacreous pigments such as titanium mica with iron oxides, titanium mica with ferric blue or with chromium oxide, titanium mica with an organic pigment of the abovementioned type, and also those based on bismuth oxychloride.

Pigmentary pastes of organic pigment are used more particularly, such as the products sold by the company Hoechst under the name:
Jaune Cosmenyl 10G: Pigment Yellow 3 (CI 11710);
Jaune Cosmenyl G: Pigment Yellow 1 (CI 11680);
Orange Cosmenyl GR: Pigment Orange 43 (CI 71105)
Rouge Cosmenyl R: Red 4 Pigment (CI 12085)
Carmin Cosmenyl FB: Red 5 Pigment (CI 12490)
Violet Cosmenyl RL: Violet Pigment 23 (CI 51319)
Bleu Cosmenyl A2R: Blue 15.1 Pigment (CI 74260)
Vert Cosmenyl GG: Green 7 Pigment (CI 74260)
Noir Cosmenyl R: Black 7 Pigment (CI 77266)

The term "direct dye" means natural and/or synthetic dyes, other than oxidation dyes. These are dyes that will spread superficially on the fibre.

These direct dyes are chosen, for example, from neutral, acidic or cationic nitrobenzene direct dyes, neutral, acidic or cationic azo direct dyes, tetraazapentamethine dyes, neutral, acidic or cationic quinone and in particular anthraquinone dyes, azine direct dyes, triarylmethane direct dyes, azomethine direct dyes and natural direct dyes.

Among the nitrobenzene direct dyes that may be mentioned, in a non-limiting manner, are the following compounds:
1,4-diamino-2-nitrobenzene, 1-amino-2 nitro-4-β-hydroxyethylaminobenzene, 1-amino-2 nitro-4-bis(β-hydroxyethyl)aminobenzene, 1,4-bis(β-hydroxyethylamino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(β-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(β-hydroxyethylamino)-4-nitrobenzene, 1-amino-2-tris(hydroxymethyl)methylamino-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-di hydroxypropyloxy-3-methylamino-4-nitrobenzene, 1-β-hydroxyethylamino-4-β,γ-di hydroxypropyloxy-2-nitrobenzene, 1-β,γ-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-bis(β-hydroxyethyl)amino-3-nitrobenzene, 1-β-hydroxyethylamino-2-nitrobenzene, 1-hydroxy-4-β-hydroxyethylamino-3-nitrobenzene.

Among the azo direct dyes, mention may be made of the cationic azo dyes described in patent applications WO-95/15144, WO-95/01772 and EP-714 954, the content of which forms an integral part of the invention.

Among these compounds, mention may be made most particularly of the following dyes: 1,3-dimethyl-2[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]pyridinium methyl sulfate.

Among the azo direct dyes, mention may also be made of the following dyes, described in the Colour Index International 3rd edition:
Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis((3-hydroxyethyl)aminobenzene and 4-hydroxy-3-(2-methoxyphenylazo)-1-naphthalenesulfonic acid.

Among the quinone direct dyes that may be mentioned are the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes that may be mentioned are the following compounds:
Basic Blue 17 and Basic Red 2.

Among the triarylmethane dyes, mention may be made of the following compounds: Basic Green 1, Acid Blue 9, Basic Violet 3, Basic Violet 14, Basic Blue 7, Acid Violet 49, Basic Blue 26, Acid Blue 7.

Among the azomethine dyes that may be mentioned are the following compounds:
2-amino-5-(4-aminophenylamino)-6-(4-aminophenylimino)-6H pyridin-3-one-2-[(4-aminophenyl)amino]-4-[(4-aminophenyl)imino]-5-hydroxycyclohexa-2,5-dien-1-one
5-hydroxy-2-[(4-hydroxyphenyl)amino]-4-[(4-hydroxyphenyl)imino]cyclohexa-2,5-dien-1-one
2-({4-[bis(2-hydroxyethyl)amino]phenyl}amino)-4-({4-[bis(2-hydroxyethypamino]phenyl}imino)-5-hydroxycyclohexa-2,5-dien-1-one
5-amino-2-[(4-aminophenyl)amino]-4-[(4-aminophenyl)imino]cyclohexa-2,5-dien-1-one
5-amino-2-[(4-hydroxyphenyl)amino]-4-[(4-hydroxyphenyl)imino]cyclohexa-2,5-dien-1-one
5-amino-2-({4-[bis(2-hydroxyethyl)amino]phenyl}amino)-4-({4-[bis(2-hydroxyethypamino]phenyl}imino)cyclohexa-2,5-dien-1-one
2-[(4-aminophenyl)amino]-5-[(2-hydroxyethyl)amino]benzo-1,4-quinone
2-[(2-hydroxyethyl)amino]-5-[(4-hydroxyphenyl)amino]benzo-1,4-quinone
2-({4-[bis(2-hydroxyethyl)amino]phenyl}amino)-5-[(2-hydroxyethyl)amino]benzo-1,4-quinone
2-amino-5-[(4-hydroxyphenyl)amino]-6-[(4-hydroxyphenyl)imino]pyridin-3(6H)-one 2-amino-5-({4-[bis(2-hydroxyethyl)amino]phenyl}amino)-6-({4-[bis(2-hydroxyethyl)amino]phenyl}imino)pyridin-3(6H)-one 3-amino-4-[(4-aminophenyl)imino]-2-chloro-6-methylcyclohexa-2,5-dien-1-one 3-amino-4-[(4-amino-3-methylphenyl)imino]-2-chloro-6-methylcyclohexa-2,5-dien-1-one 3-amino-4-[(4-amino-2-methylphenyl)imino]-2-chloro-6-methylcyclohexa-2,5-dien-1-one 14+75151

3-amino-2-chloro-4-[(4-hydroxyphenyl)imino]-6-methylcyclohexa-2,5-dien-1-one 808+75151

3-amino-4-({4-[bis(2-hydroxyethyl)amino]phenyl}imino)-2-chloro-6-methylcyclohexa-2,5-dien-1-one.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and especially henna-based poultices or extracts, may also be used.

The pigments are present in concentrations preferably ranging from 0.05% to 10% by weight and even more particularly from 0.1% to 3% by weight relative to the total weight of the composition.

The direct dyes and/or pigments that may be used in the composition of the invention are dyes that are sparingly soluble or insoluble in water or aqueous-alcoholic medium, known to those skilled in the art. Examples that may be mentioned include:

| Dye | Chemical structure |
|---|---|
| Solvent Black 3 | 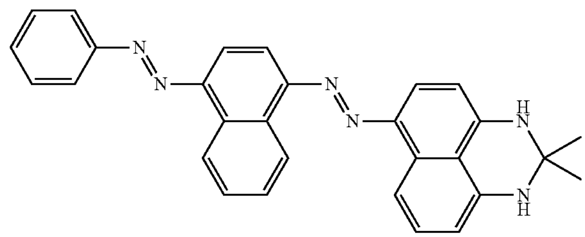 [SMILES: CC1(C)Nc2cccc3c(/N=N/c4ccc(/N=N/c5ccccc5)c5ccccc45)ccc(c23)N1] |
| Solvent Blue 104 | 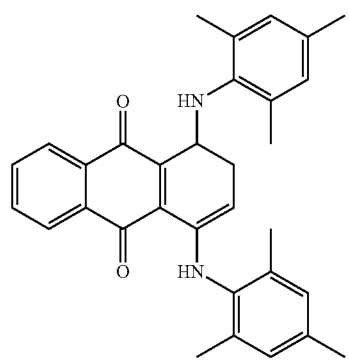 [SMILES: Cc1cc(C)c(NC2=CCC(Nc3c(C)cc(C)cc3C)C3=C2C(=O)c2ccccc2C3=O)c(C)c1] |
| Disperse Blue 134 | 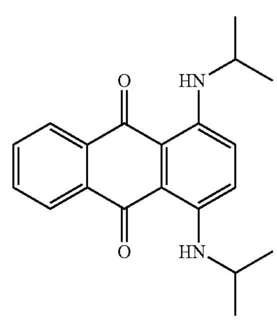 [SMILES: CC(C)Nc1ccc(NC(C)C)c2c1C(=O)c1ccccc1C2=O] |
| Solvent Blue 14 | 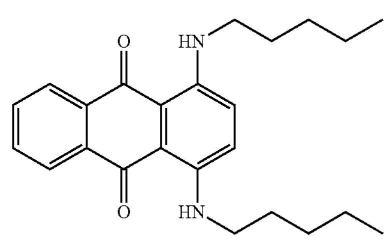 [SMILES: CCCCCNc1ccc(NCCCCC)c2c1C(=O)c1ccccc1C2=O] |

-continued

| Dye | Chemical structure |
|---|---|
| Disperse Blue 14 | 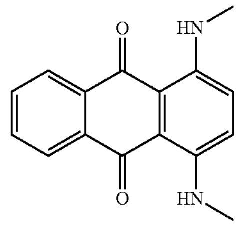 [SMILES: CNc1ccc(NC)c2c1C(=O)c1ccccc1C2=O] |
| Solvent Red 2 | 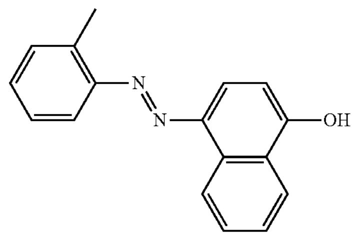 [SMILES: Cc1ccccc1/N=N/c1ccc(O)c2ccccc12] |
| Solvent Brown 5 | 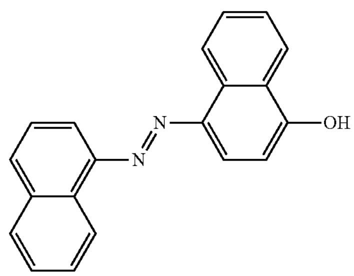 [SMILES: Oc1ccc(/N=N/c2cccc3ccccc23)c2ccccc12] |
| Solvent Green 5 | 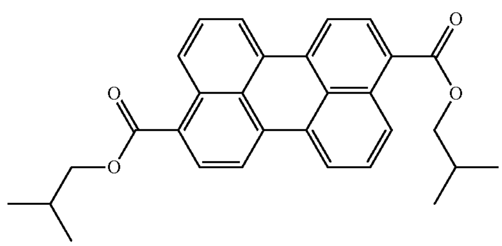 [SMILES: CC(C)COC(=O)c1ccc2c3cccc4c(C(=O)OCC(C)C)ccc(c5cccc1c52)c43] |
| Solvent Orange 2 | 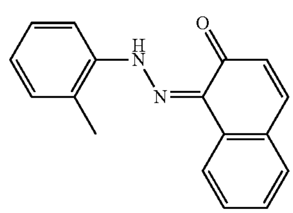 [SMILES: Cc1ccccc1N/N=C1\C(=O)C=Cc2ccccc21] |
| Solvent Orange 1 | 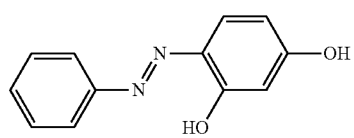 [SMILES: Oc1ccc(/N=N/c2ccccc2)c(O)c1] |
| Disperse Orange 24 | 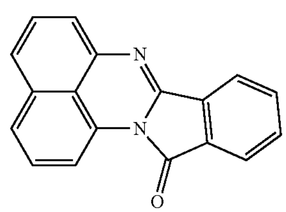 [SMILES: O=C1c2ccccc2C2=Nc3cccc4cccc(c34)N12] |

-continued

| Dye | Chemical structure |
|---|---|
| Solvent Orange 63 | 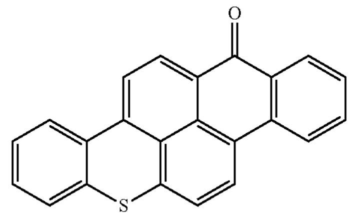 [SMILES: O=c1c2ccccc2c2ccc3sc4ccccc4c4ccc1c2c34] |
| Solvent Red 49 | 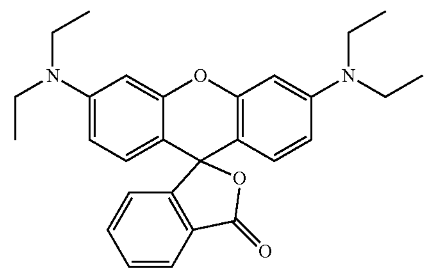 [SMILES: CCN(CC)c1ccc2c(c1)Oc1cc(N(CC)CC)ccc1C21OC(=O)c2ccccc21] |
| Solvent Red 1 | 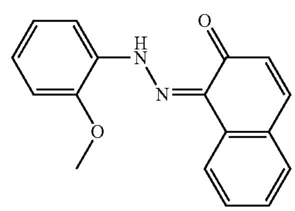 [SMILES: COc1ccccc1N/N=C1\C(=O)C=Cc2ccccc21] |
| Solvent Red 26 | 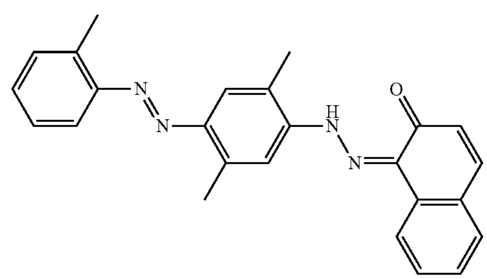 [SMILES: Cc1ccccc1/N=N/c1cc(C)c(N/N=C2\C(=O)C=Cc3ccccc32)cc1C] |
| Solvent Red 27 | 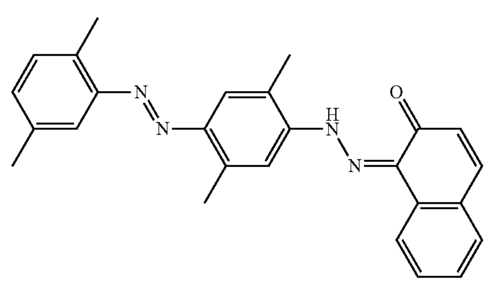 [SMILES: Cc1ccc(C)c(/N=N/c2cc(C)c(N/N=C3\C(=O)C=Cc4ccccc43)cc2C)c1] |
| Solvent Red 18 | 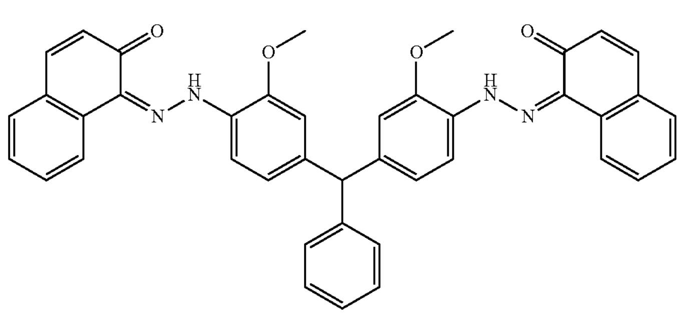 [SMILES: COc1cc(C(c2ccccc2)c2ccc(N/N=C3\C(=O)C=Cc4ccccc43)c(OC)c2)ccc1N/N=C1\C(=O)C=Cc2ccccc21] |

-continued

| Dye | Chemical structure |
|---|---|
| Solvent Red 23 | 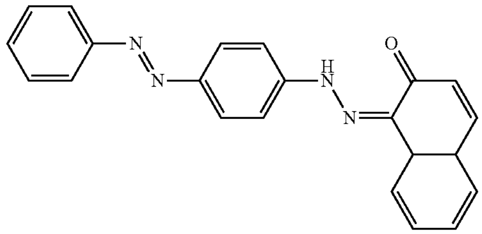 [SMILES: O=C1C=CC2C=CC=CC2/C1=N/Nc1ccc(/N=N/c2ccccc2)cc1] |
| Solvent Red 4 | 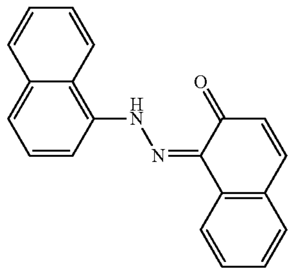 [SMILES: O=C1C=Cc2ccccc2/C1=N/Nc1cccc2ccccc12] |
| Solvent Orange 7 | 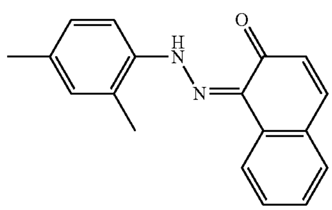 [SMILES: Cc1ccc(N/N=C2\C(=O)C=Cc3ccccc32)c(C)c1] |
| Disperse Blue 72 | 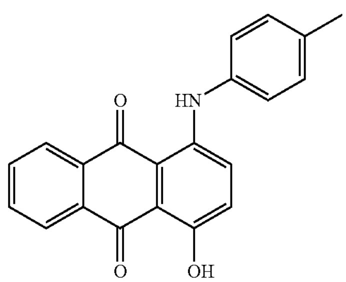 [SMILES: Cc1ccc(Nc2ccc(O)c3c2C(=O)c2ccccc2C3=O)cc1] |
| Disperse Violet 26 | 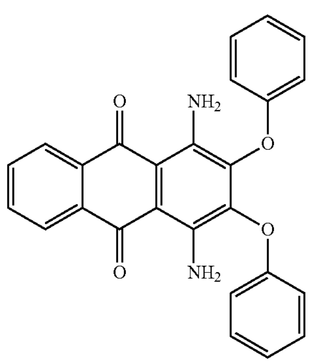 [SMILES: Nc1c(Oc2ccccc2)c(Oc2ccccc2)c(N)c2c1C(=O)c1ccccc1C2=O] |
| Disperse Yellow 16 | 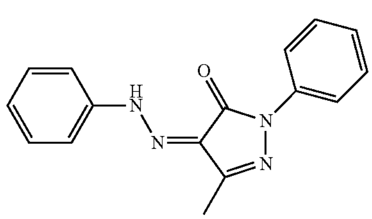 [SMILES: CC1=NN(c2ccccc2)C(=O)/C1=N\Nc1ccccc1] |

-continued

| Dye | Chemical structure |
|---|---|
| Disperse Yellow 82 | 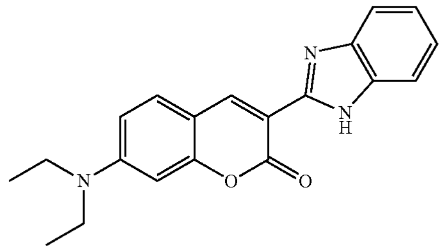 [SMILES: CCN(CC)c1ccc2cc(-c3nc4ccccc4[nH]3)c(=O)oc2c1] |
| Disperse Yellow 54 | 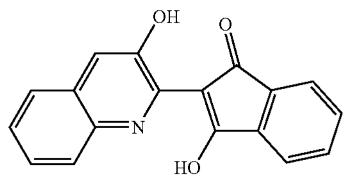 [SMILES: O=C1C(c2nc3ccccc3cc2O)=C(O)c2ccccc21] |
| Solvent Yellow 29 | 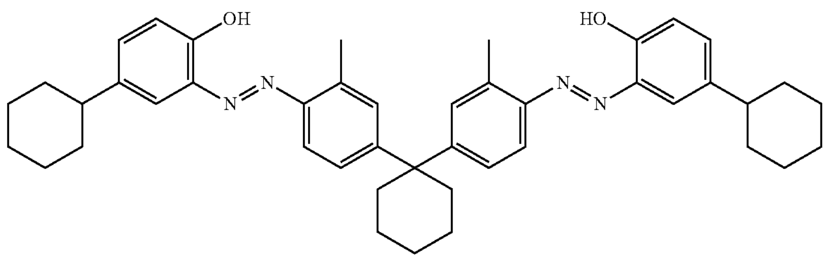 [SMILES: Cc1cc(C2(c3ccc(/N=N/c4cc(C5CCCCC5)ccc4O)c(C)c3)CCCCC2)ccc1/N=N/c1cc(C2CCCCC2)ccc1O] |
| Solvent Yellow 163 | 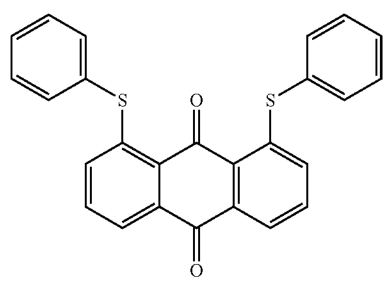 [SMILES: O=C1c2cccc(Sc3ccccc3)c2C(=O)c2c(Sc3ccccc3)cccc21] |
| Solvent Yellow 3 | 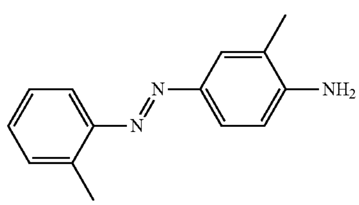 [SMILES: Cc1cc(/N=N/c2ccccc2C)ccc1N] |
| Solvent Yellow 56 | 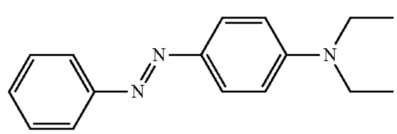 [SMILES: CCN(CC)c1ccc(/N=N/c2ccccc2)cc1] |
| Solvent Yellow 18 | 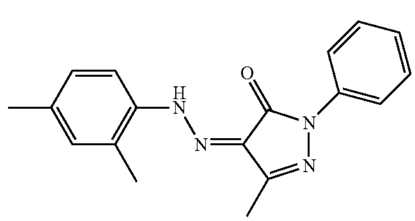 [SMILES: CC1=NN(c2ccccc2)C(=O)/C1=N\Nc1ccc(C)cc1C] |

-continued

| Dye | Chemical structure |
|---|---|
| Solvent Yellow 98 | (structure: thioxanthene-fused naphthalimide with N-(CH$_2$)$_{17}$CH$_3$) |
| Solvent Yellow 12 | (structure: o-tolyl-N=N-(2-hydroxy-5-methylphenyl) azo dye) |
| Solvent Yellow 14 | (structure: 1-(phenylhydrazono)naphthalen-2(1H)-one) |
| Disperse Red 13 | (structure: 2-chloro-4-nitrophenyl azo coupled to 4-[N-ethyl-N-(2-hydroxyethyl)amino]phenyl) |
| Disperse Green 9 | (structure: 3,5-dinitrothiophen-2-yl azo coupled to 2-acetamido-4-(diethylamino)phenyl) |
| Disperse Blue 148 | (structure: 5-nitro-benzisothiazol-3-yl azo coupled to 4-[N-ethyl-N-(2-acetoxyethyl)amino]phenyl) |
| Disperse Violet 63 | (structure: 2,4-dinitrophenyl azo coupled to 2-(chloroacetamido)-4-(diethylamino)phenyl, with CN substituent) |

| Dye | Chemical structure |
|---|---|
| Disperse Blue 60 | 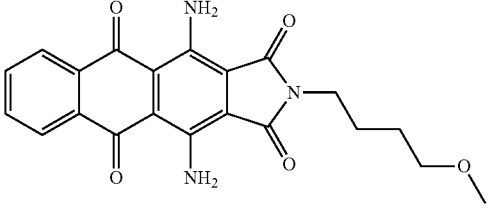 [SMILES: COCCCCn1c(=O)c2c(N)c3c(=O)c4ccccc4c(=O)c3c(N)c2c1=O] |
| Solvent Orange 15 | 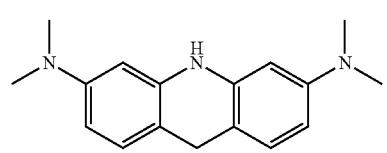 |

Preferably, the pigments and/or dyes that are sparingly soluble or insoluble in standard aqueous-alcoholic supports such as water, and especially the pigment(s) and/or direct dye(s) with a solubility of less than 20 grams per liter of water, are chosen from carbon black:

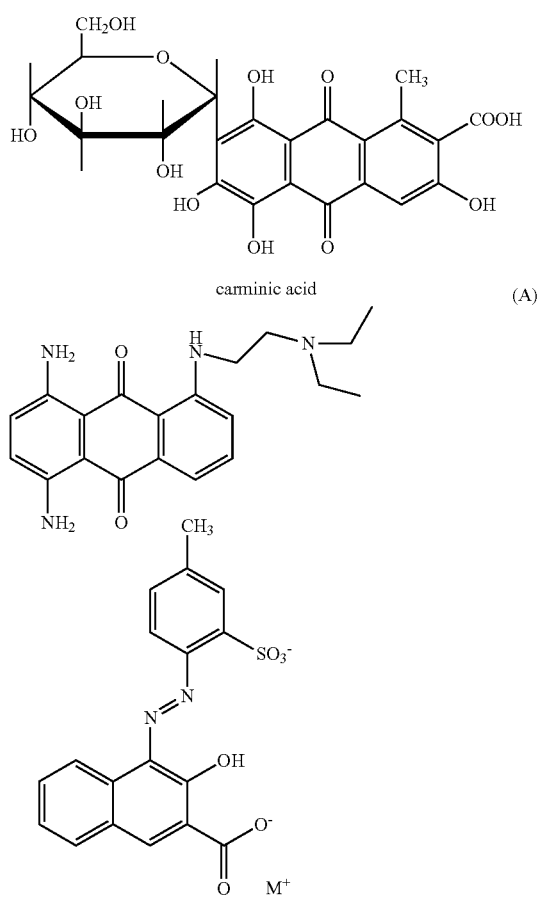

(A'), with M+ representing a cationic counterion, particularly an alkali metal or alkaline-earth metal, preferentially an alkaline-earth metal such as $Ca^{++}$

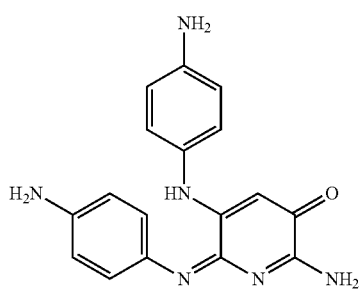

Carminic acid, the compounds (A), (A') and (B) and also the organic or mineral acid or base salts thereof, optical isomers thereof: stereoisomers or enantiomers and diastereoisomers, geometrical isomers and tautomers thereof, and solvates thereof such as hydrates.

The hydrophobic direct dye(s) may be present in the composition in an amount of between 0.001% and 5% by weight approximately relative to the total weight of the composition.

Cosmetic Composition:

According to on particular embodiment the dye(s) or pigment(s) according to the invention are other than phthalocyanins, and more particularly the dye(s) or pigment(s) according to the invention are other than phthalocyanins comprising copper when the compound of formula (I) is such as:

X represents OH, $R_3$ and $R_4$ represent H, $A_1$ represents H, $R_1$ is substituted by the group (E), $R'_3$ and $R'_4$ represent H and X' represents OH; or X represents OH, and $R_3$ and $R_4$ represent H, $A_1$ represents the group (G), $R''_3$ and $R''_4$ represent H and X'' represents OH.

The cosmetic composition according to the invention is cosmetically acceptable for dyeing keratin fibres, i.e. it comprises a dye support that generally contains water or a mixture of water and of one or more organic solvents or a mixture of organic solvents. Preferentially, the cosmetic composition of the invention contains water.

The cosmetic composition according to the invention is cosmetically acceptable for dyeing keratin fibres, i.e. it comprises a dye support that generally contains water or a mixture of water and of one or more organic solvents or a mixture of organic solvents. Preferentially, the cosmetic composition of the invention contains water.

As mentioned previously, the dye support is aqueous-alcoholic. This support preferentially contains only water. According to one particularly advantageous embodiment of the invention, the cosmetic composition is formed i) from at least one compound of formula (I) as defined previously, ii) from at least one pigment or direct dye as defined previously, and iii) from water.

The term "organic solvent" means an organic substance that is capable of dissolving or dispersing in another substance without chemically modifying it.

Organic Solvents:

Examples of organic solvents that may be mentioned include C1-C4 lower alcohols, such as ethanol and isopropanol; polyols and polyol ethers such as 2-butoxyethanol, propylene glycol, dipropylene glycol, propylene glycol monomethyl ether, diethylene glycol monoethyl ether and monomethyl ether, hexylene glycol, and also aromatic alcohols, for instance benzyl alcohol or phenoxyethanol.

The organic solvents are present in proportions preferably of between 1% and 40% by weight approximately and even more preferentially between 5% and 30% by weight approximately relative to the total weight of the dye composition.

According to one particular embodiment of the invention, the composition contains as support water and no organic solvents other than those of formula (I) or (Ia) and as defined previously.

Adjuvants:

The composition(s) of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these optional additional compound(s) such that the advantageous properties intrinsically associated with the composition in accordance with the invention are not, or are not substantially, adversely affected by the envisaged addition(s).

Additional Dyes:

The composition comprising one or more pigments and/or one or more direct dyes that are sparingly soluble or insoluble in aqueous-alcoholic solvents as defined previously may also comprise one or more additional direct dyes. These direct dyes are chosen, for example, from those conventionally used in direct dyeing, and among which mention may be made of any commonly used aromatic and/or non-aromatic dye such as neutral, acidic or cationic nitrobenzene direct dyes, neutral, acidic or cationic azo direct dyes, natural direct dyes other than direct dyes for pigments that are sparingly soluble or insoluble in aqueous-alcoholic solvents, neutral, acidic or cationic quinone and in particular anthraquinone direct dyes, azine, triarylmethane, indoamine, methine, styryl, porphyrin, metalloporphyrin, phthalocyanine, cyanine and methine direct dyes, and fluorescent dyes.

Among the natural direct dyes, mention may be made of lawsone, juglone, indigo, isatin, curcumin, spinulosin, apigenidin and orceins. Extracts or decoctions containing these natural dyes and especially henna-based poultices or extracts, may also be used.

The additional direct dye(s) used in the composition preferably represent from 0.001% to 10% by weight approximately relative to the total weight of the composition(s), and even more preferentially from 0.05% to 5% by weight approximately.

The cosmetic composition according to the invention comprising one or more direct dye derivatives and/or one or more pigments that are sparingly soluble or insoluble in aqueous-alcoholic solvents as defined previously may also use or comprise one or more oxidation bases and/or one or more couplers conventionally used for the dyeing of keratin fibres.

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols, naphthalene-based couplers and heterocyclic couplers, and the addition salts thereof.

The oxidation base(s) present in the dye composition(s) are each generally present in an amount of between 0.001% and 10% by weight relative to the total weight of the corresponding compositions.

According to another particular embodiment of the invention, the composition according to the invention does not contain any oxidation base.

According to yet another embodiment, the composition does not contain any coupler. Preferentially, the composition according to the invention does not contain any oxidation base or any couplers of aromatic amine type.

The cosmetic composition of the invention may be in various galenical forms, such as a powder, a lotion, a mousse, a cream or a gel, or in any other form that is suitable for dyeing keratin fibres. It may also be conditioned in a pump-dispenser bottle without propellant or under pressure in an aerosol can in the presence of a propellant and form a foam.

pH of the Composition

According to one particular mode of the invention, the pH of the composition containing the pigment(s) and/or the direct dye(s) that are sparingly soluble or insoluble in aqueous-alcoholic solvents is between 3 and 12, particularly between 3 and 9.5 and even more preferentially between 3 and 8.

The pH of the composition according to the invention may be adjusted to the desired value by means of acidifying or basifying agents usually used in the dyeing of keratin fibres, or alternatively using standard buffer systems.

Among the acidifying agents for the compositions used in the invention, examples that may be mentioned include mineral or organic acids, for instance hydrochloric acid, orthophosphoric acid or sulfuric acid, carboxylic acids, for instance acetic acid, tartaric acid, citric acid and lactic acid, and sulfonic acids.

Basifying Agent

The basifying agent may be aqueous ammonia. Preferentially, the basifying agent is chosen from alkanolamines such as monoethanolamine, diethanolamine and triethanolamine, alkali metal carbonate salts, guanidine, imidazole, sodium hydroxide, potassium hydroxide or calcium hydroxide, arginine, and the compounds of formula (II) below:

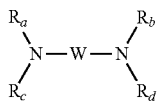

(II)

in which formula (II):
W is a propylene residue optionally substituted with a hydroxyl group or a $C_1$-$C_4$ alkyl radical;
$R_a$, $R_b$, $R_c$ and $R_d$, which may be identical for different, represent a hydrogen atom or a $C_1$-$C_4$ alkyl or $C_1$-$C_4$ hydroxyalkyl radical.

More particularly, the basifying agent(s) are chosen from ethanolamine, carbonate salts, guanidine, imidazole, calcium hydroxide and arginine.

Dyeing Process in One or More Steps

One subject of the invention concerns the dyeing process by treating or applying to keratin fibres i) one or more compounds of formula (I) or (I') as defined previously and ii) one or more pigments and/or one or more direct dyes that are sparingly soluble or insoluble in aqueous-alcoholic solvents, the ingredients i) and ii) possibly being applied to the materials either simultaneously in one step, or successively in several steps.

According to one preferred mode of the dyeing process of the invention, the ingredients i) and ii) are applied in one step. In this case, preferentially, the ingredients i) and ii) are together in a cosmetic composition, which is then applied to the keratin materials.

According to another particular mode of the dyeing process of the invention, the ingredients i) and ii) are applied successively. In this case, preferentially, ingredient i) is in one cosmetic composition, and ingredient ii) is in another cosmetic composition. According to a first advantageous variant of the invention, the cosmetic composition comprising ingredient i) is applied in a first step to the keratin materials, and a cosmetic composition comprising ingredient ii) is then applied in a second step. According to another variant of the invention, the cosmetic composition comprising ingredient ii) is applied in a first step to the keratin materials, and a cosmetic composition comprising ingredient i) is then applied in a second step.

According to one preferred mode of the process according to the invention, the process does not use any oxidation bases or couplers.

The leave-on time for coloration to be achieved is between 3 and 120 minutes. Preferentially, after application of the composition containing the direct dye(s) and/or the pigment(s) that are sparingly soluble or insoluble in aqueous-alcoholic solvents, the composition is left to act for 10 to 60 minutes.

Irrespective of the application method, the application temperature is generally between room temperature and 80° C. and more particularly between 15° C. and 45° C. Thus, it is advantageously possible, after application of the composition(s) comprising ingredients i) and ii) as defined previously, to subject the head of hair to a heat treatment by heating to a temperature of between 30 and 60° C. In practice, this operation may be performed using a styling hood, a hairdryer, an infrared ray dispenser or other standard heating appliances.

A heating iron at a temperature of between 60 and 220° C. and preferably between 120 and 200° C. may be used, both as heating means and as hair straightening means.

One particular mode of the invention concerns a dyeing process that is performed at room temperature (25° C.).

After applying ingredients i) and ii) as defined previously to the keratin fibres, the said locks are preferentially rinsed with water, washed with standard shampoo and dried by means that have been described previously.

According to a particular dyeing process of the invention, the composition comprising ingredients i) and ii) is applied in a single step to the keratin fibres, particularly the hair, and is then left on for between 15 and 60 minutes, preferentially 30 minutes, and the said fibres are then rinsed with water, washed with standard shampoo and dried.

In all the particular modes and variants of the processes described previously, the compositions mentioned are ready-to-use compositions that may result from the extemporaneous mixing of two or more compositions and especially of compositions present in dyeing kits.

Dyeing Device or "Kit":

Another subject of the invention is a multi-compartment dyeing device or "kit". Advantageously, this device comprises from 2 to 5 compartments containing from 2 to 5 compositions in which are distributed the following ingredients:
i) one or more compounds of formula (I) or (I') as defined previously, and
ii) one or more pigments and/or one or more direct dyes that are sparingly soluble or insoluble in aqueous-alcoholic solvents.

The compositions of the device according to the invention are conditioned in separate compartments, optionally accompanied by suitable application means, which may be identical or different, such as fine brushes, coarse brushes or sponges.

This device mentioned above may also be equipped with a means for dispensing the desired mixture on the hair, such as the devices described in patent FR 2 586 913.

The non-limiting examples that follow illustrate the invention without limiting its scope.

EXAMPLES OF DYEING

The dyes or pigments (A), (B), and 1-n-butyl-4-hydroxycarbonylpyrrolidin-2-one belonging to formula (I) are commercially available or may be prepared via the standard methods known to those skilled in the art starting with commercial reagents.

Example 1

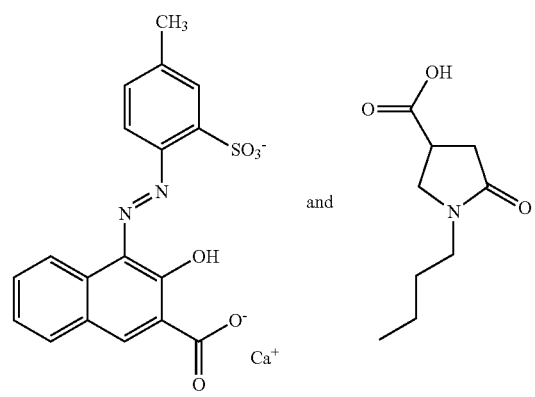

(A)

The following compositions were prepared (amounts expressed in g %)

|  | Composition 1 (invention) | Composition 1c (comparative) |
|---|---|---|
| 1-Butyl-5-oxopyrrolidine-3-carboxylic acid | 5 | — |
| Ethanol | 15 | 15 |
| Hydroxyethylcellulose | 1.6 | 1.6 |
| Sodium lauryl ether sulfate | 5 | 5 |
| Dye A | 2 | 2 |
| Water | qs 100 | qs 100 |

Each composition is applied to locks of natural hair containing 90% white hairs, for 30 minutes at 30° C.

After applying and leaving to stand on the locks, the locks are rinsed, shampooed and dried. The lock dyed with composition 1 is dyed a raspberry red colour.

The colour of the locks was evaluated in the CIE L*a*b* system, using a Konica-Minolta CM2600d spectrocolorimeter.

The ΔE colour uptake is calculated from the measured L*a*b* values. In this L*a*b* system, L* represents the intensity of the colour, a* indicates the green/red colour axis and b* the blue/yellow colour axis.

The lower the value of L*, the darker or more intense the colour.

The colour uptake on the keratin fibres is evaluated according to ΔE, which is the colour variation between natural dyed fibres and natural undyed fibres; the greater the "uptake", the more the fibres are dyed.

$$\Delta E = \sqrt{(L^* - L_o^*)^2 + (a^* - a_o^*)^2 + (b^* - b_o^*)^2}$$

In this equation, L*, a* and b* represent the values measured on the dyed keratin fibres and $L_o^*$, $a_o^*$ and $b_o^*$ represent the values measured on the undyed keratin fibres.

Measurement Results:

The uptakes after coloration using the composition according to the invention (composition 1) and that of the comparative composition (composition 1c) were compared as follows:

|  | L* (D65) | a* (D65) | b* (D65) | Colour "uptake" ΔE |
|---|---|---|---|---|
| Undyed lock | 51.86 | 1.68 | 12.87 |  |
| Lock dyed with composition 1 (invention) | 40.58 | 23.66 | 8.54 | 25.09 |
| Lock dyed with composition 1c (comparative) | 53.69 | 14.4 | 7.63 | 13.64 |

The uptake on the keratin fibres is significantly greater with composition 1 of the invention containing the pyrrolidine derivative of formula (I) or (Ia), the lock dyed with this composition is much more intense, powerful and chromatic (red) than the lock dyed with the comparative composition 1c.

Example 2

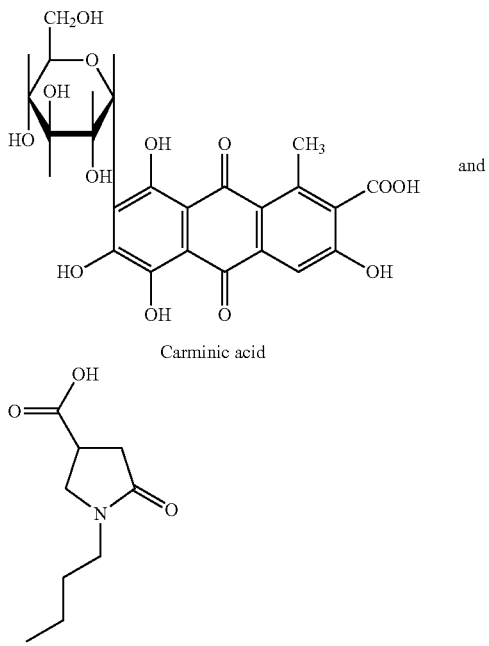

Carminic acid

The following compositions were prepared (amounts expressed in g %)

|  | Composition 2 (invention) | Composition 2c (comparative) |
|---|---|---|
| 1-Butyl-5-oxopyrrolidine-3-carboxylic acid | 7 | — |
| Carminic acid | 2 | 2 |
| Water | qs 100 | qs 100 |

Each composition is applied to locks of natural hair containing 90% white hairs, for 30 minutes at 30° C.

After applying and leaving to stand on the locks, the locks are rinsed, shampooed and dried. The lock dyed with composition 2 is dyed a pink colour.

Measurement Results:

The uptakes after coloration using the composition according to the invention (composition 2) and that of the comparative composition (composition 2c) were compared as follows:

|  | L* (D65) | a* (D65) | b* (D65) | Colour "uptake" ΔE |
|---|---|---|---|---|
| Undyed lock | 56.64 | 0.55 | 13.01 |  |
| Lock dyed with composition 2 (invention) | 47.5 | 14.18 | 9.8 | 16.72 |
| Lock dyed with composition 2c (comparative) | 48.63 | 1.4 | 10.18 | 8.54 |

The uptake on the keratin fibres is significantly greater with composition 2 of the invention containing the pyrrolidine derivative of formula (I) or (Ia), the lock dyed with this composition is much more intense, powerful and chromatic (pink) than the lock dyed with the comparative composition 2c.

The invention claimed is:
1. A method for dyeing keratin fibers comprising applying to the keratin fibers:
i) at least one compound of formula (I):

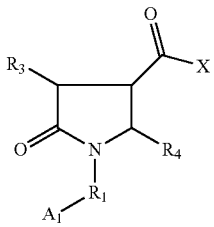

(I)

and the organic or mineral acid or base salts thereof, optical isomers thereof, stereoisomers, enantiomers and diastereoisomers thereof, geometrical isomers and tautomers thereof, and solvates and hydrates thereof;
wherein in formula (I):
X is chosen from hydroxyl (—OH) and amino (—NH$_2$) groups;
R$_1$ is chosen from:
a) optionally substituted hydrocarbon-based chains, wherein the chain is chosen from saturated linear C$_1$-C$_{30}$ or branched C$_3$-C$_{30}$ or cyclic C$_3$-C$_7$ chains; and wherein the hydrocarbon-based chain is optionally interrupted with:
  i) at least one entity chosen from —O—, —N(R$_6$)— or —S—;
  ii) at least one group chosen from —S(O)—, —S(O)$_2$—, —C(O)—, —N$^+$(R$_6$)(R$_7$)—, and combinations of i) and ii); and/or
  iii) 3- to 6-membered saturated or unsaturated carbon-based rings optionally substituted with at least one identical or different radical chosen from hydroxyl (—OH) and amino (—NRR') groups;
b) divalent chains -Cycl-Alk-Cycl'- wherein:
  Cycl and Cycl', which may be identical or different, are chosen from cyclic hydrocarbon-based chains; and
  Alk is chosen from optionally substituted or unsubstituted (C$_1$-C$_6$) alkylene chains; and
c) optionally substituted hydrocarbon-based chains, wherein the chain is chosen from saturated linear C$_2$-C$_{30}$ or branched C$_3$-C$_{30}$ or cyclic C$_3$-C$_7$ chains; and wherein the hydrocarbon-based chain is optionally interrupted with:
  i) at least one entity chosen from —O—, —N(R$_6$)— or —S—;
  ii) at least one group chosen from —S(O)—, —S(O)$_2$—, —C(O)—, —N$^+$(R$_6$)(R$_7$)—, and combinations of i) and ii); and/or
  iii) 3- to 6-membered saturated or unsaturated carbon-based rings optionally substituted with at least one identical or different radical chosen from hydroxyl (—OH) and amino (—NRR') groups;

R$_1$ may be substituted with at least one radical of formula (E):

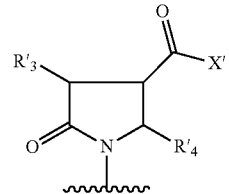

(E)

wherein in formula (E):
X' is chosen from hydroxyl (—OH) and amino (—NH$_2$) groups;

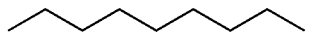

represents the point of attachment of the radical (E) to the rest of the molecule;
A$_1$ is chosen from hydrogen and groups chosen from
a) —OH, b) —SH, c) —NRR', d) —O—P(O)(OH)$_2$, e) —O—S(O)$_2$OH, f) —S(O)$_2$OH, g) —C(O)OH, h) saturated or unsaturated 3- to 6-membered (hetero)cycles optionally substituted with at least one identical or different radical chosen from (hydroxy)(C$_1$-C$_6$) alkyl, hydroxyl and —NRR', the (hetero)cycle possibly being cationic, i) —N$^+$(R$_7$)(R$_8$)(R$_9$), j) RR'N—C(=NR")—N(R)— and

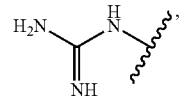

and
k) radicals of formula (G):

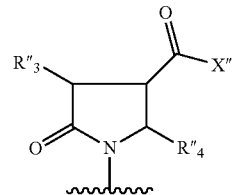

(G)

wherein in formula (G), X" is chosen from hydroxyl (—OH) and amino (—NH$_2$) groups;
R$_3$, R$_4$, R'$_3$, R'$_4$, R"$_3$ and R"$_4$, which may be identical or different, are chosen from hydrogen and linear C$_1$-C$_{12}$ or branched C$_3$-C$_{12}$ alkyl chains;
R$_6$ is chosen from hydrogen and linear (C$_1$-C$_{20}$)alkyl or branched (C$_3$-C$_{20}$)alkyl groups, optionally substituted with a radical (G);
R$_7$, R$_8$ and R$_9$, which may be identical or different, are chosen from hydrogen and (C$_1$-C$_6$) alkyl groups optionally substituted with at least one hydroxyl group;

R, R' and R", which may be identical or different, are chosen from hydrogen and ($C_1$-$C_{18}$) alkyl groups optionally substituted with at least one hydroxyl group;

wherein when $A_1$ and/or $R_1$ contain or denote a cationic group, the electrical neutrality of the compounds of formula (I) is ensured by an anionic counterion or a mixture of anionic counterions; and ii) at least one colorant chosen from pigments and direct dyes, wherein the colorant is sparingly soluble or insoluble in standard aqueous-alcoholic supports.

2. The method according to claim 1, wherein $R_3$, $R_4$, $R'_3$, $R'_4$, $R''_3$ and $R''_4$ are hydrogen.

3. The method according to claim 1, wherein $R_1$ is chosen from saturated linear $C_1$-$C_{20}$ or branched $C_3$-$C_{20}$ hydrocarbon-based chains optionally interrupted with at least one entity chosen from O, S, —N($R_6$)—, $N^+$($R_6$)($R_7$)—, —N($R_6$)—C(O)—, —C(O)—N($R_6$)—, —N($R_6$)—C(O)—N($R_7$)— and —S—S—; and/or $R_1$ is optionally substituted with at least one identical or different radical chosen from hydroxyl (—OH) and —NRR'.

4. The method according to claim 1, wherein $R_1$ is a divalent group chosen from those of formula —[O—$CH_2$—$CH_2$]$_n$—O—, wherein n is an integer ranging from 1 to 4 inclusive.

5. The method according to claim 1, wherein $R_6$ is chosen from ($C_1$-$C_6$) alkyl groups optionally substituted with a radical (G) and $R_7$ is chosen from hydrogen and ($C_1$-$C_6$) alkyl groups.

6. The method according to claim 1, wherein $A_1$ is chosen from:
hydrogen,
OH,
$S(O)_2OH$,
NRR',
—O—$P(O)OH_2$,
—O—$S(O)_2OH$,
C(O)OH,
saturated or unsaturated 4- to 6-membered (hetero)cycles, the (hetero)cycles possibly being cationic, and
radicals of formulae —$N^+$($R_6$)($R_7$)($R_8$) or (G).

7. The method according to claim 1, wherein the compounds of formula (I) comprise at least one cationic group.

8. The method according to claim 1, wherein the compounds of formula (I) comprise only one 2-pyrrolidinone unit functionalized in position 4 with a carboxylic acid or amide and do not comprise any units (E) or (G).

9. The method according to claim 1, wherein X is OH, $R_3$ and $R_4$ and $A_1$ are hydrogen; and $R_1$ is chosen from linear $C_1$-$C_8$ or branched $C_3$-$C_8$ alkylene groups.

10. The method according to claim 1, wherein the compounds of formula (I) comprise two or three 2-pyrrolidinone units functionalized in position 4 with a carboxylic acid or amide; wherein $R_1$ is chosen from divalent chains -alk-T-alk'- wherein:
T is chosen from:
a covalent bond σ,
heteroatoms,
N(R) groups, wherein R is chosen from hydrogen, ($C_1$-$C_6$) alkyl groups and -alk"-(E) groups; and
divalent groups —$X_a$-alk"-$X_b$— wherein $X_a$ and $X_b$, which may be identical or different, are chosen from heteroatoms and NH groups;
-alk, alk' and alk", which may be identical or different, are chosen from ($C_1$-$C_6$) alkylene groups; and
$A_1$ is a radical (G).

11. The method according to claim 1, wherein the compounds of formula (I) are chosen from compounds of formula (I'):

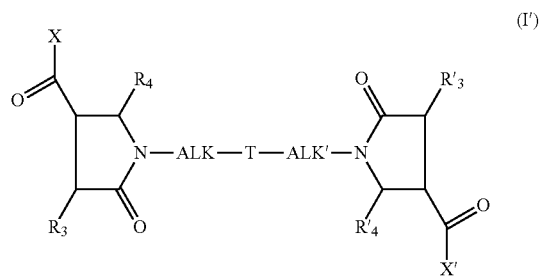

wherein in formula (I'):
T is chosen from:
a covalent bond σ,
heteroatoms,
N(R) groups, wherein R is chosen from hydrogen and ($C_1$-$C_6$) alkyl groups and -alk"-(G) groups; or
divalent groups —$X_a$-alk"-$X_b$— wherein $X_a$ and $X_b$, which may be identical or different, are chosen from heteroatoms and NH groups; and
alk, alk' and alk", which may be identical or different, are chosen from ($C_1$-$C_6$) alkylene groups.

12. The method according to claim 1, wherein the compounds of formula (I) are chosen from compounds a to bo and 1 to 24, the organic or mineral acid or base salts thereof, optical isomers thereof, stereoisomers, enantiomers and diastereoisomers thereof, and the solvates and hydrates thereof:

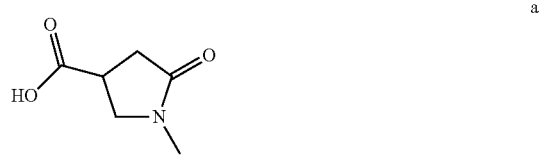

a

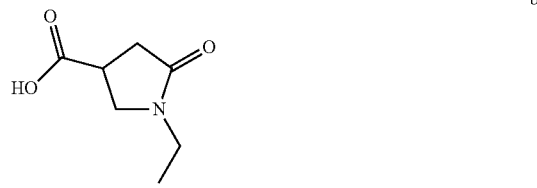

b

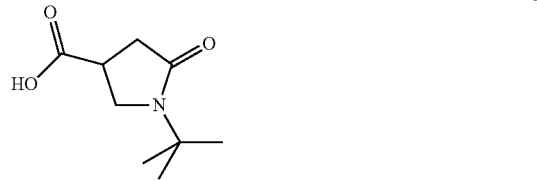

c

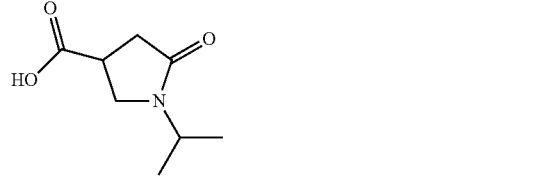

d

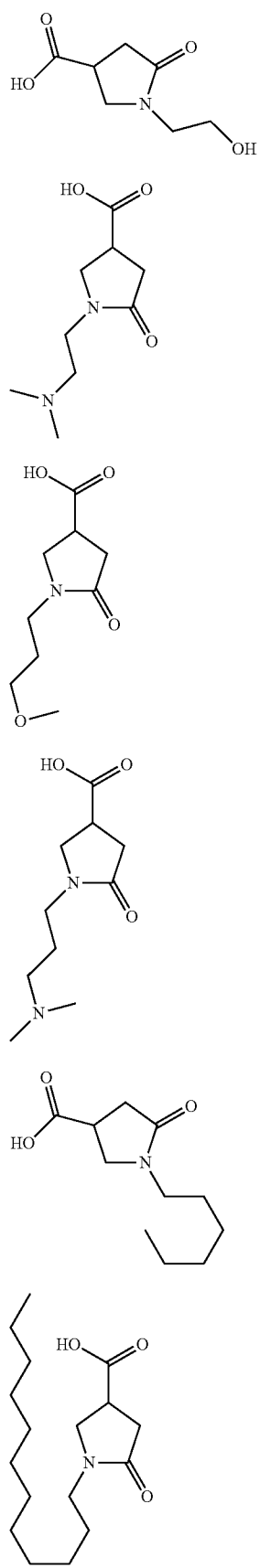
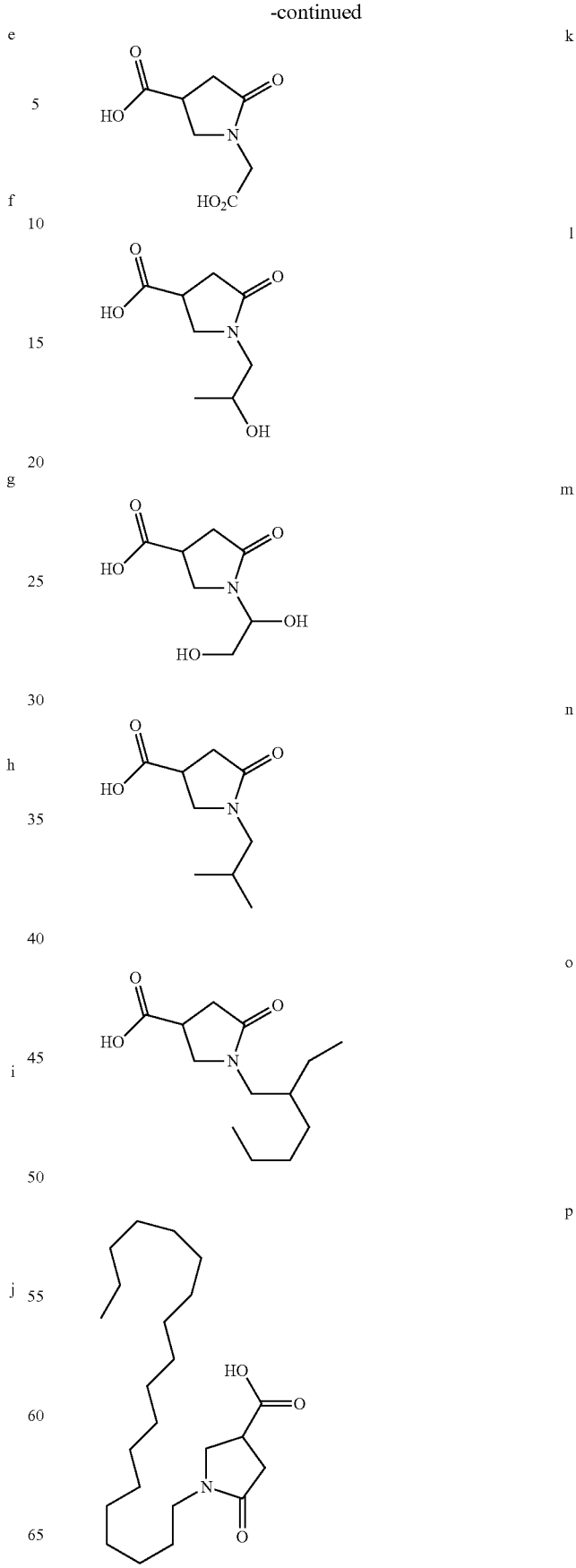

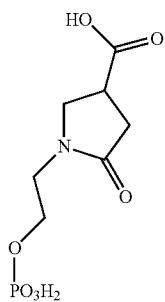
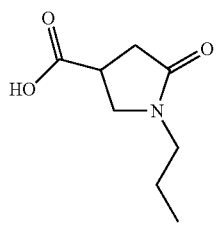
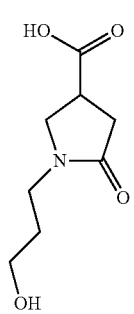
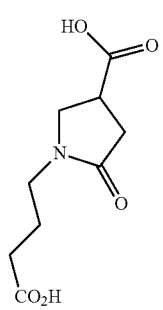
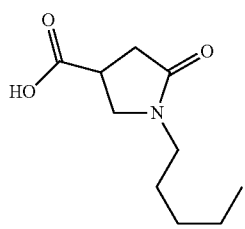
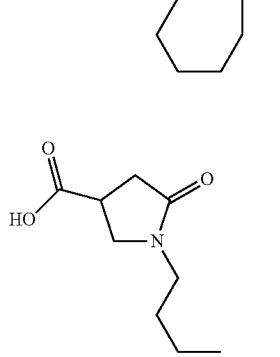

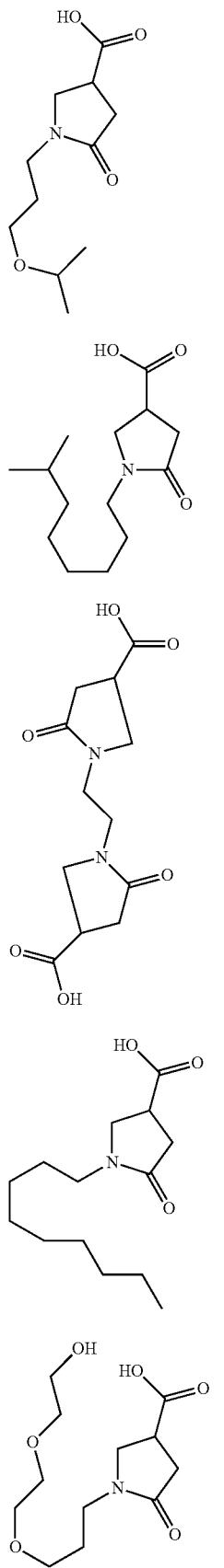
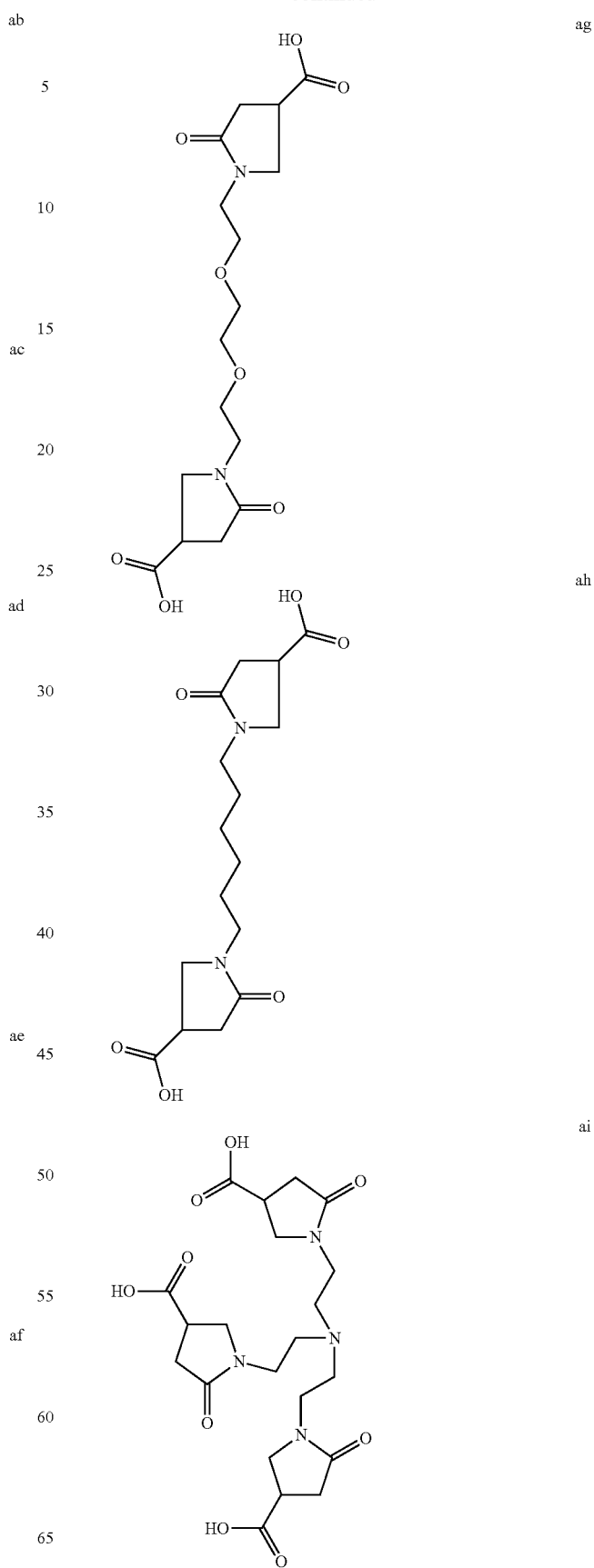

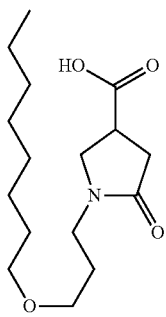
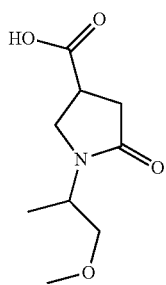
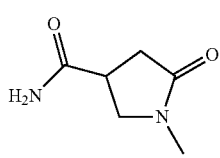
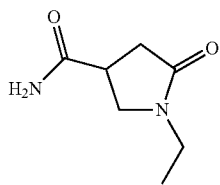
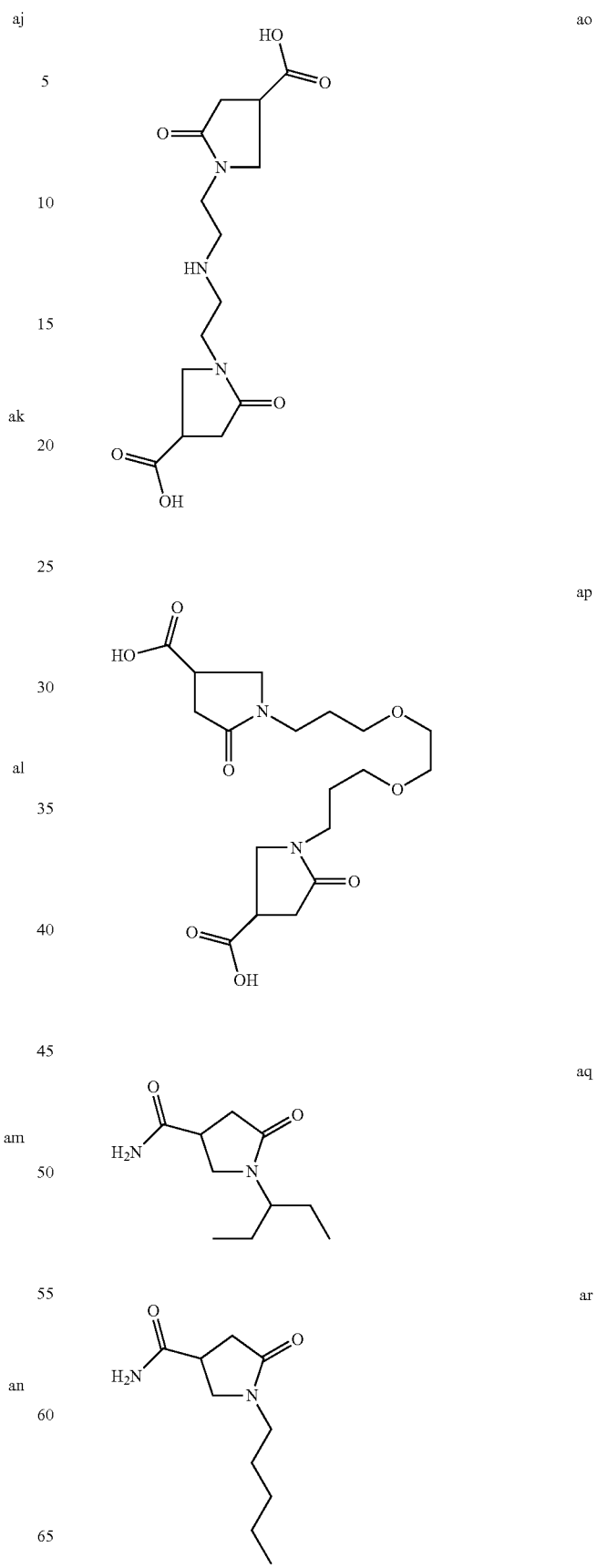

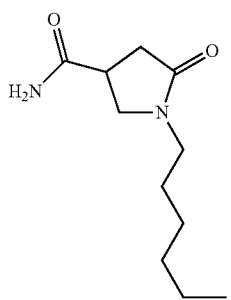
as
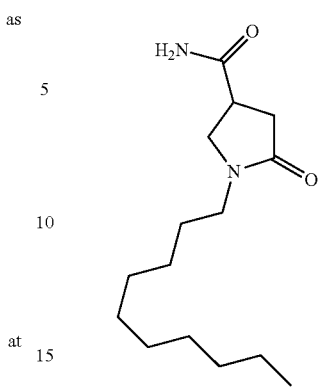
ax
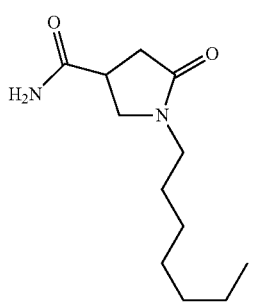
at
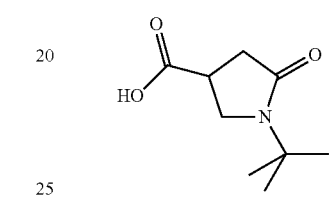
ay
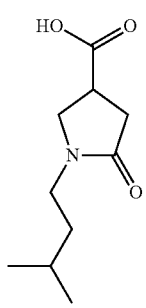
au
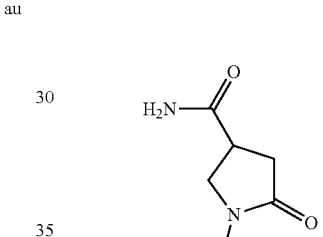
az
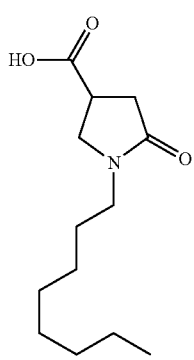
av
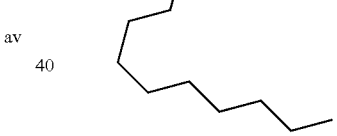
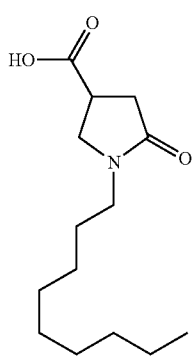
aw
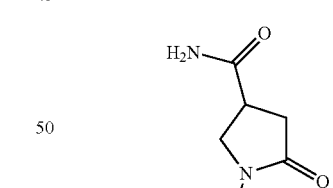
ba
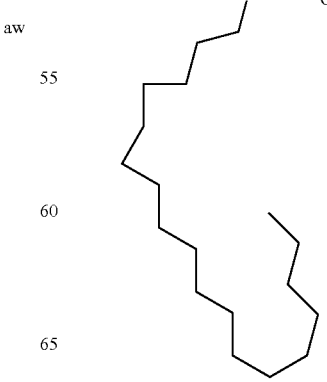

71
-continued
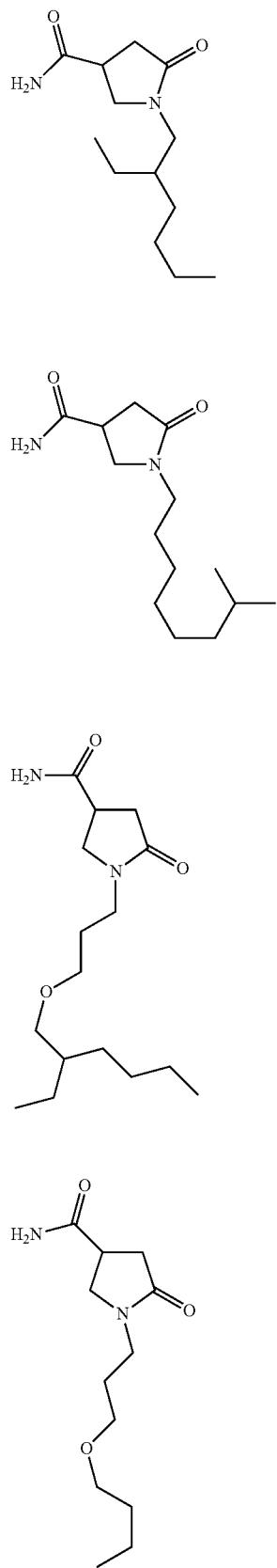
72
-continued
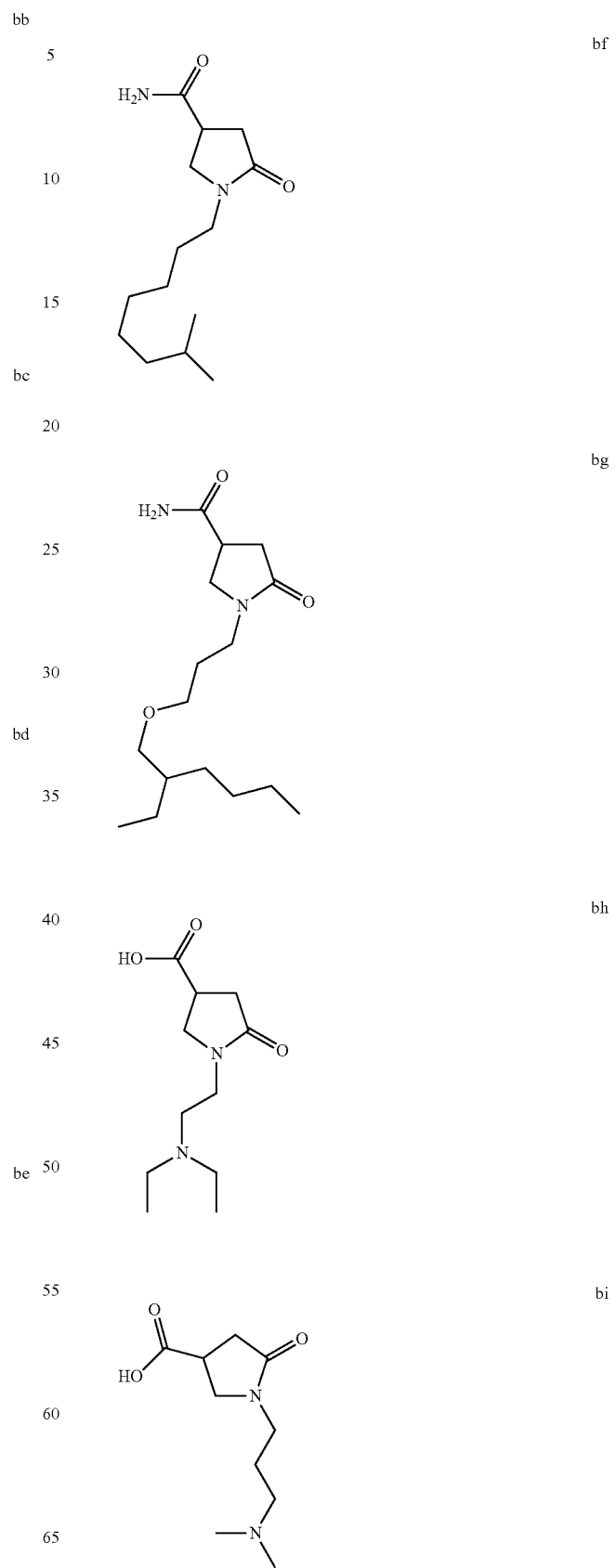

-continued
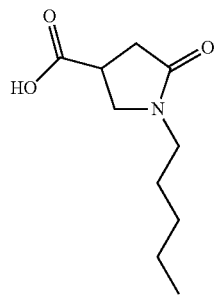
bj
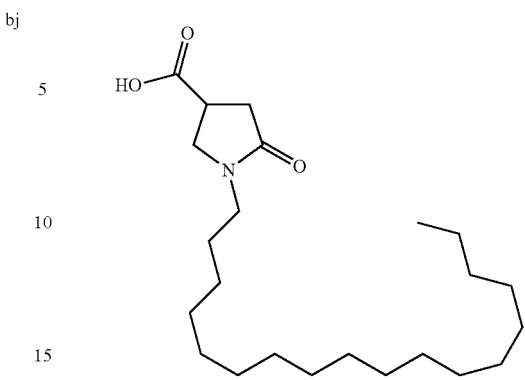
bo
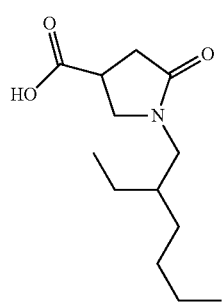
bk
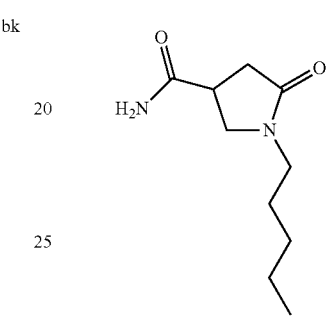
1
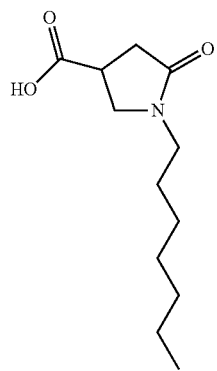
bl
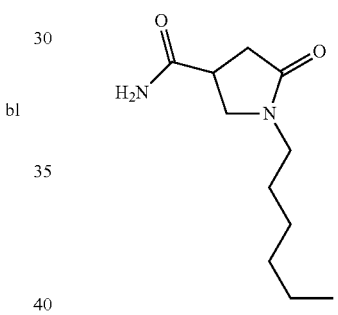
2
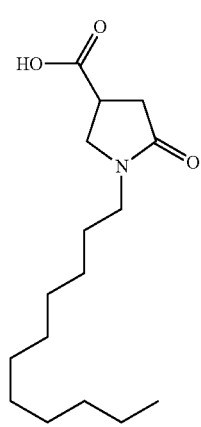
bn
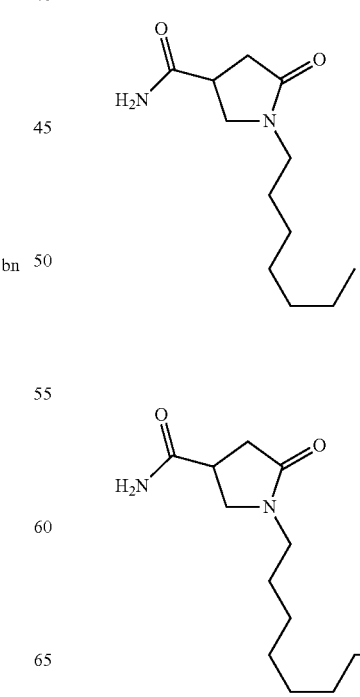
3
4

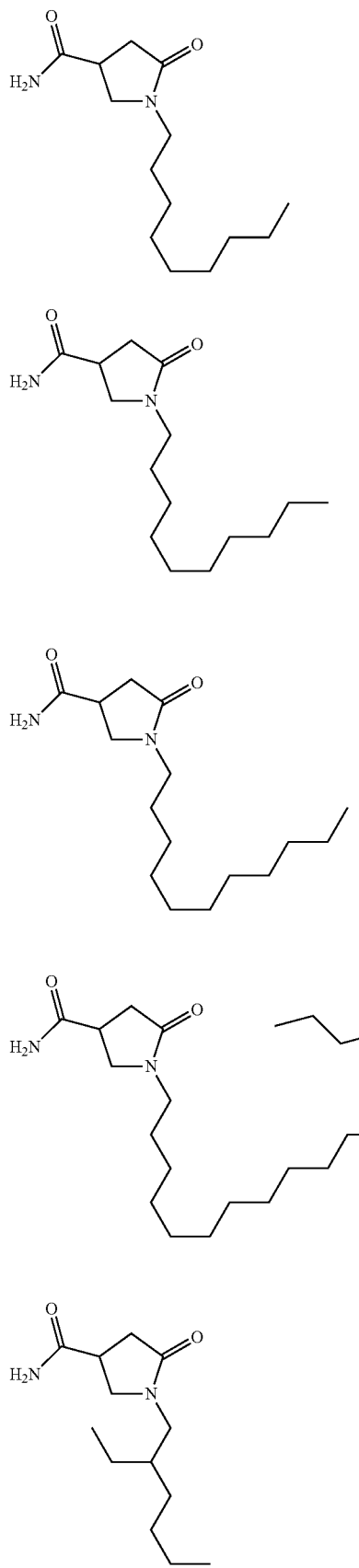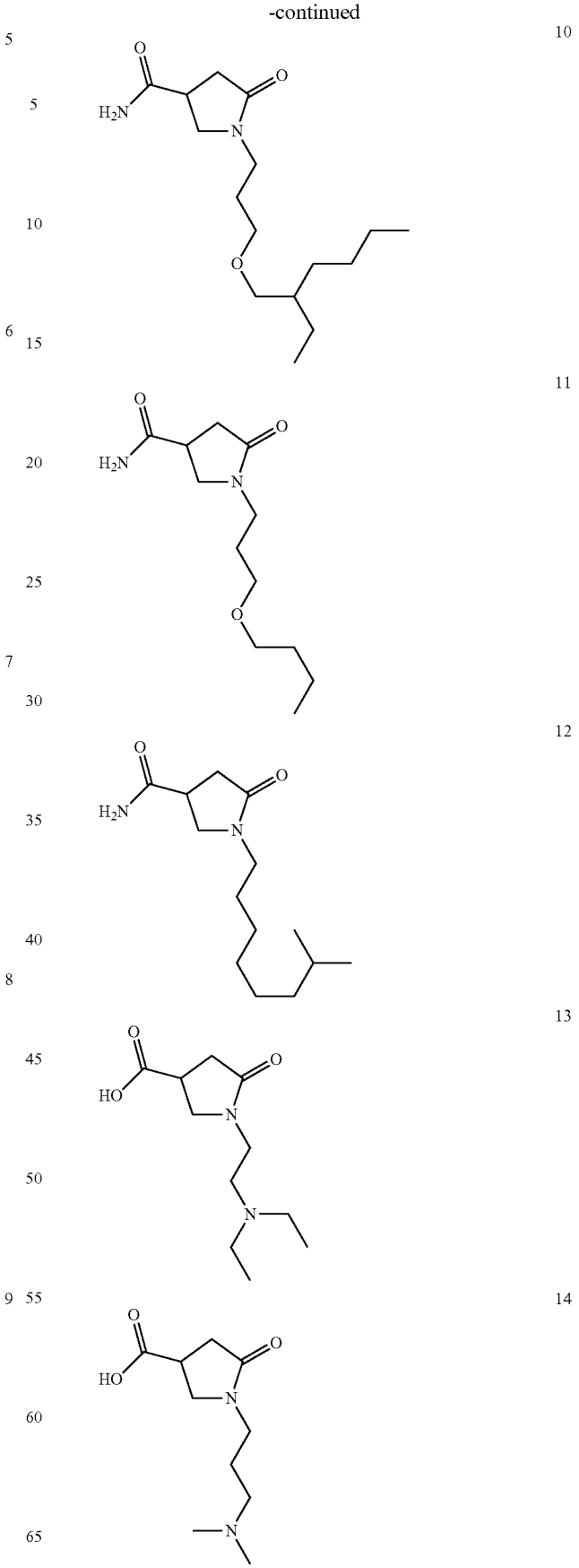

15

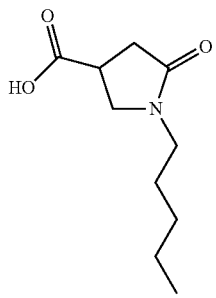

16

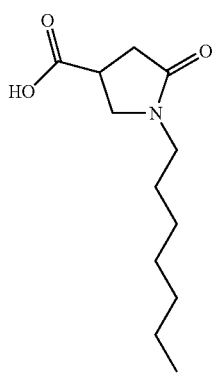

17

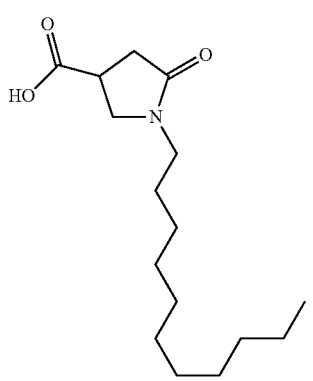

18

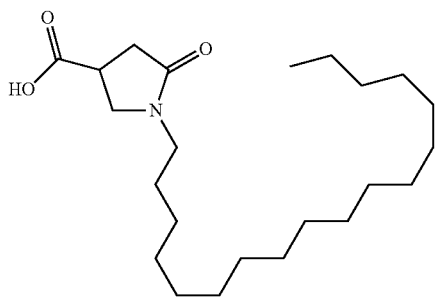

19

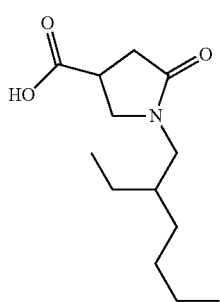

20

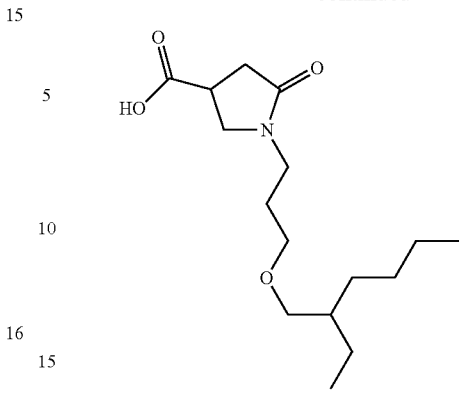

21

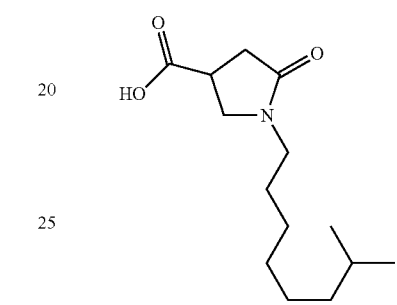

22

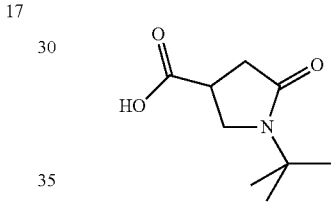

23

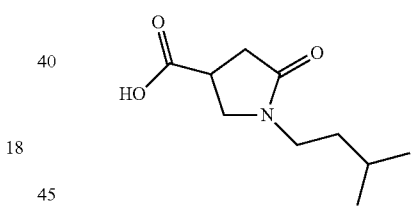

24

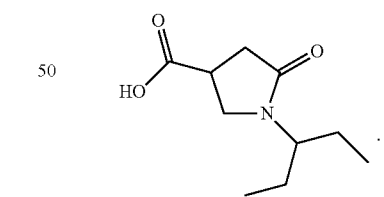

13. The method according to claim 1, wherein the at least one colorant ii) is chosen from neutral, acidic or cationic nitrobenzene direct dyes, neutral, acidic or cationic azo direct dyes, tetraazapentamethine dyes, neutral, acidic or cationic quinone and anthraquinone dyes, azine direct dyes, triarylmethane direct dyes, azomethine direct dyes, and natural direct dyes.

14. The method according to claim 1, wherein the components i) and ii) are applied to the fibers simultaneously in one step or successively in several steps.

15. A composition comprising, in a suitable cosmetic medium:
   i) at least one compound of formula (I) as defined in claim 1; and
   ii) at least one colorant chosen from pigments and direct dyes that are that are sparingly soluble or insoluble in standard aqueous-alcoholic supports;
   with the proviso that the compounds of formula (I) are not chosen from compounds (a) or (b) when the at least one colorant ii) is chosen from azo black type dyes:

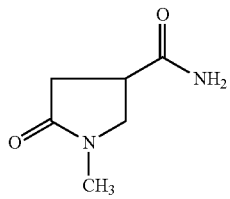
(a)

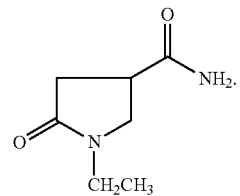
(b)

16. A 2-pyrrolidinone compound functionalized in position 4 with a carboxylic acid or amide of formula (I) chosen from compounds of formulae 1 to 12, 14, 17, and 19 to 24, as defined in claim 12.

17. A method for improving the color uptake on keratin fibers of at least one colorant chosen from direct dyes and pigments that are sparingly soluble or insoluble in standard aqueous alcoholic supports, the method comprising applying to the keratin fibers i) the least one colorant and ii) a 2-pyrrolidinone compound functionalized in position 4 with a carboxylic acid or amide of formula (I) as defined in claim 1.

* * * * *